United States Patent
Babakhani et al.

(10) Patent No.: US 11,911,625 B2
(45) Date of Patent: Feb. 27, 2024

(54) SYSTEMS AND METHODS FOR CONTROLLING WIRELESSLY POWERED LEADLESS PACEMAKERS

(71) Applicants: The Regents of the University of California, Oakland, CA (US); Texas Heart Institute, Houston, TX (US)

(72) Inventors: Aydin Babakhani, Los Angeles, CA (US); Hongming Lyu, Shanghai (CN); Razavi Mehdi, Houston, TX (US); Mathews M. John, Houston, TX (US); Allison Post, Houston, TX (US)

(73) Assignees: The Regents of the University of California, Oakland, CA (US); Texas Heart Institute, Houston, TX (US)

( * ) Notice: Subject to any disclaimer, the term of this patent is extended or adjusted under 35 U.S.C. 154(b) by 150 days.

(21) Appl. No.: 17/295,005

(22) PCT Filed: Nov. 20, 2019

(86) PCT No.: PCT/US2019/062443
§ 371 (c)(1),
(2) Date: May 18, 2021

(87) PCT Pub. No.: WO2020/106862
PCT Pub. Date: May 28, 2020

(65) Prior Publication Data
US 2022/0008736 A1 Jan. 13, 2022

Related U.S. Application Data

(60) Provisional application No. 62/845,619, filed on May 9, 2019, provisional application No. 62/769,984, filed on Nov. 20, 2018.

(51) Int. Cl.
*A61N 1/375* (2006.01)
*A61N 1/368* (2006.01)
(Continued)

(52) U.S. Cl.
CPC ......... *A61N 1/3756* (2013.01); *A61N 1/3684* (2013.01); *A61N 1/3787* (2013.01); *A61N 1/37288* (2013.01); *A61N 1/37512* (2017.08)

(58) Field of Classification Search
CPC .............. A61N 1/3756; A61N 1/37512; A61N 1/3684; A61N 1/37288; A61N 1/3787
See application file for complete search history.

(56) References Cited

U.S. PATENT DOCUMENTS

| | | | |
|---|---|---|---|
| 4,388,927 A | 6/1983 | Schober | |
| 4,612,940 A | 9/1986 | Kasevich et al. | |

(Continued)

FOREIGN PATENT DOCUMENTS

| | | | |
|---|---|---|---|
| CN | 104767291 A | 7/2015 | |
| CN | 113228464 A | 8/2021 | |

(Continued)

OTHER PUBLICATIONS

Paul, "Inductance: loop and partial", John Wiley & Sons, 2011, 395 pgs., presented in two parts.

(Continued)

*Primary Examiner* — Tammie K Marlen
(74) *Attorney, Agent, or Firm* — KPPB LLP

(57) ABSTRACT

Systems and methods for heart stimulation in accordance with embodiments of the invention are illustrated. One embodiment includes a heart stimulation system, including a first wirelessly powered, leadless pacemaker, including a wireless power receiver tuned to a first frequency, an energy harvesting circuitry, a stimulation circuitry, and a stimulation electrode, a controller, including a wireless power signal generator, a wireless power transmitter tuned to the frequency, a processor, and a memory containing a stimulation control application, where the stimulation control application directs the processor to generate a power transfer signal (Continued)

using the first wireless power signal generator, and transmit the power transfer signal using the wireless power transmitter, wherein the wirelessly powered, leadless pacemaker receives the power transfer signal using the first wireless power receiver, and when receiving the power transfer signal, the energy harvesting circuitry stores power received via the wireless power receiver in at least one capacitor.

21 Claims, 13 Drawing Sheets

(51) Int. Cl.
*A61N 1/372* (2006.01)
*A61N 1/378* (2006.01)

(56) References Cited

U.S. PATENT DOCUMENTS

| | | | |
|---|---|---|---|
| 4,719,919 A | 1/1988 | Marchosky et al. |
| 5,464,429 A | 11/1995 | Hedberg et al. |
| 5,522,865 A | 6/1996 | Schulman et al. |
| 5,630,426 A | 5/1997 | Eggers et al. |
| 5,749,909 A | 5/1998 | Schroeppel et al. |
| 6,402,689 B1 | 6/2002 | Scarantino et al. |
| 6,423,056 B1 | 7/2002 | Ishikawa et al. |
| 6,735,472 B2 | 5/2004 | Helland |
| 6,813,518 B2 | 11/2004 | Kuepper |
| 6,870,503 B2 | 3/2005 | Mohamadi |
| 6,882,315 B2 | 4/2005 | Richley et al. |
| 7,010,340 B2 | 3/2006 | Scarantino et al. |
| 7,043,301 B1 | 5/2006 | Kroll et al. |
| 7,132,173 B2 | 11/2006 | Daulton |
| 7,177,341 B2 | 2/2007 | Mccorkle |
| 7,228,228 B2 | 6/2007 | Bartlett et al. |
| 7,339,883 B2 | 3/2008 | Santhoff et al. |
| 7,610,092 B2 | 10/2009 | Cowan et al. |
| 7,751,881 B2 | 7/2010 | Cowan et al. |
| 8,032,227 B2 | 10/2011 | Parramon et al. |
| 8,126,418 B2 | 2/2012 | Nowak et al. |
| 8,188,841 B2 | 5/2012 | Dowla et al. |
| 8,290,600 B2 | 10/2012 | Hastings et al. |
| 8,547,248 B2 | 10/2013 | Zdeblick et al. |
| 8,552,597 B2 | 10/2013 | Song et al. |
| 8,634,919 B1 | 1/2014 | Hou et al. |
| 8,644,933 B2 | 2/2014 | Ozawa et al. |
| 8,670,824 B2 | 3/2014 | Anderson et al. |
| 8,939,928 B2 | 1/2015 | Savoie et al. |
| 9,026,212 B2 | 5/2015 | Imran |
| 9,031,658 B2 | 5/2015 | Chiao et al. |
| 9,037,223 B2 | 5/2015 | Oral et al. |
| 9,153,642 B2 | 10/2015 | Li et al. |
| 9,161,693 B2 | 10/2015 | Rizwan |
| 9,168,380 B1 | 10/2015 | Greenhut et al. |
| 9,168,383 B2 | 10/2015 | Jacobson et al. |
| 9,205,258 B2 | 12/2015 | Simon et al. |
| 9,270,137 B2 | 2/2016 | Greene |
| 9,277,874 B2 | 3/2016 | Joshi et al. |
| 9,421,369 B2 | 8/2016 | Liu et al. |
| 9,423,438 B2 | 8/2016 | Lin et al. |
| 9,486,621 B2 | 11/2016 | Howard et al. |
| 9,522,270 B2 | 12/2016 | Perryman et al. |
| 9,544,068 B2 | 1/2017 | Arbabian et al. |
| 9,669,223 B2 | 6/2017 | Auricchio et al. |
| 9,669,230 B2 | 6/2017 | Koop |
| 9,685,793 B2 | 6/2017 | Zargham et al. |
| 9,700,712 B2 | 7/2017 | Towe |
| 9,711,978 B2 | 7/2017 | Manova-elssibony et al. |
| 9,953,195 B2 | 4/2018 | Turner et al. |
| 10,014,730 B2 | 7/2018 | Nayak |
| 10,238,872 B2 | 3/2019 | Pivonka et al. |
| 10,312,743 B2 | 6/2019 | Ouda et al. |
| 10,369,369 B2 | 8/2019 | Perryman et al. |
| 10,493,288 B2 | 12/2019 | Hastings et al. |
| 10,530,421 B2 | 1/2020 | Muthali et al. |
| 10,537,403 B2 | 1/2020 | Vora et al. |
| 10,742,222 B2 | 8/2020 | Emira et al. |
| 10,978,917 B2 | 4/2021 | Freitas et al. |
| 11,048,893 B2 | 6/2021 | Babakhani et al. |
| 11,050,263 B2 | 6/2021 | Bae et al. |
| 11,071,857 B2 | 7/2021 | Sun et al. |
| 11,515,733 B2 | 11/2022 | Babakhani et al. |
| 11,712,559 B2 | 8/2023 | Sun et al. |
| 2002/0064245 A1 | 5/2002 | McCorkle |
| 2002/0103507 A1 | 8/2002 | Helland |
| 2002/0137991 A1 | 9/2002 | Scarantino et al. |
| 2003/0032986 A1 | 2/2003 | Kupper |
| 2004/0054471 A1 | 3/2004 | Bartlett et al. |
| 2004/0058186 A1 | 3/2004 | Daulton |
| 2004/0095287 A1 | 5/2004 | Mohamadi |
| 2004/0108954 A1 | 6/2004 | Richley et al. |
| 2005/0058121 A1 | 3/2005 | Santhoff et al. |
| 2005/0256549 A1 | 11/2005 | Holzer |
| 2006/0136004 A1 | 6/2006 | Cowan et al. |
| 2007/0118187 A1 | 5/2007 | Denker et al. |
| 2007/0120677 A1 | 5/2007 | Park et al. |
| 2007/0211786 A1 | 9/2007 | Shattil |
| 2007/0225781 A1 | 9/2007 | Saadat et al. |
| 2007/0293895 A1 | 12/2007 | Cowan et al. |
| 2008/0021505 A1 | 1/2008 | Hastings et al. |
| 2008/0039904 A1* | 2/2008 | Bulkes ............... A61N 1/37512 607/116 |
| 2008/0252422 A1 | 10/2008 | Dowla et al. |
| 2008/0262580 A1 | 10/2008 | Gerber et al. |
| 2008/0300660 A1 | 12/2008 | John |
| 2008/0306359 A1 | 12/2008 | Zdeblick et al. |
| 2009/0157141 A1 | 6/2009 | Chiao et al. |
| 2009/0219139 A1 | 9/2009 | Slesinski |
| 2009/0292341 A1 | 11/2009 | Parramon et al. |
| 2010/0076517 A1 | 3/2010 | Imran |
| 2010/0114243 A1 | 5/2010 | Nowak et al. |
| 2010/0308974 A1 | 12/2010 | Rowland et al. |
| 2011/0022025 A1 | 1/2011 | Savoie et al. |
| 2011/0288615 A1 | 11/2011 | Armstrong et al. |
| 2012/0008714 A1 | 1/2012 | Rizwan |
| 2012/0109236 A1 | 5/2012 | Jacobson et al. |
| 2012/0239118 A1 | 9/2012 | Ozawa et al. |
| 2012/0256492 A1 | 10/2012 | Song et al. |
| 2013/0066400 A1 | 3/2013 | Perryman et al. |
| 2013/0109987 A1 | 5/2013 | Kunis et al. |
| 2013/0123882 A1 | 5/2013 | Towe |
| 2013/0197380 A1 | 8/2013 | Oral |
| 2014/0046389 A1 | 2/2014 | Anderson et al. |
| 2014/0058239 A1 | 2/2014 | Joshi et al. |
| 2014/0198062 A1 | 7/2014 | Kreutzer et al. |
| 2014/0243848 A1 | 8/2014 | Auricchio et al. |
| 2014/0252543 A1 | 9/2014 | Li et al. |
| 2014/0336474 A1 | 11/2014 | Arbabian et al. |
| 2014/0375261 A1 | 12/2014 | Manova-Elssibony et al. |
| 2015/0042358 A1 | 2/2015 | Lin et al. |
| 2015/0076920 A1 | 3/2015 | Zargham et al. |
| 2015/0127068 A1 | 5/2015 | Simon et al. |
| 2015/0217123 A1 | 8/2015 | Deterre et al. |
| 2015/0229139 A1 | 8/2015 | Greene |
| 2015/0297900 A1 | 10/2015 | Perryman et al. |
| 2015/0343205 A1 | 12/2015 | Howard, III et al. |
| 2015/0356332 A1 | 12/2015 | Turner et al. |
| 2016/0008602 A1 | 1/2016 | Perryman et al. |
| 2016/0038739 A1 | 2/2016 | Liu et al. |
| 2016/0048710 A1 | 2/2016 | Nekoogar et al. |
| 2016/0149441 A1 | 5/2016 | Nayak |
| 2016/0228718 A1 | 8/2016 | Koop |
| 2016/0338798 A1 | 11/2016 | Vora et al. |
| 2016/0380754 A1 | 12/2016 | Chen et al. |
| 2017/0001003 A1 | 1/2017 | Pivonka et al. |
| 2018/0069486 A1 | 3/2018 | Ouda et al. |
| 2018/0071539 A1* | 3/2018 | Hastings ............ A61N 1/37512 |
| 2018/0123639 A1 | 5/2018 | Muthali et al. |
| 2018/0177431 A1 | 6/2018 | Rottenberg |
| 2018/0235692 A1 | 8/2018 | Efimov et al. |
| 2019/0097430 A1 | 3/2019 | Bae et al. |
| 2019/0180065 A1 | 6/2019 | Babakhani et al. |
| 2019/0224476 A1 | 7/2019 | Sun et al. |
| 2019/0247050 A1 | 8/2019 | Goldsmith |

(56) References Cited

U.S. PATENT DOCUMENTS

| | | |
|---|---|---|
| 2019/0247664 A1 | 8/2019 | Irazoqui et al. |
| 2019/0262605 A1 | 8/2019 | Babakhani et al. |
| 2019/0326785 A1 | 10/2019 | Freitas et al. |
| 2020/0022607 A1 | 1/2020 | Pratt et al. |
| 2020/0155828 A1 | 5/2020 | Shepard et al. |
| 2020/0195256 A1 | 6/2020 | Emira et al. |
| 2021/0143678 A1 | 5/2021 | Georgakopoulos |
| 2021/0339017 A1 | 11/2021 | Sun et al. |
| 2021/0356417 A1 | 11/2021 | Babakhani et al. |
| 2021/0397257 A1 | 12/2021 | Rogers et al. |
| 2022/0158497 A1 | 5/2022 | Babakhani et al. |
| 2022/0252506 A1 | 8/2022 | Babakhani et al. |
| 2022/0264196 A1 | 8/2022 | Lyu et al. |
| 2022/0273944 A1 | 9/2022 | Werneth et al. |
| 2022/0379124 A1 | 12/2022 | Babakhani et al. |
| 2023/0081364 A1 | 3/2023 | Babakhani et al. |
| 2023/0181910 A1 | 6/2023 | Werneth |

FOREIGN PATENT DOCUMENTS

| | | |
|---|---|---|
| EP | 3884562 A1 | 9/2021 |
| EP | 4110165 A1 | 1/2023 |
| JP | 2002505930 A | 2/2002 |
| JP | 2008516741 A | 5/2008 |
| JP | 2010527267 A | 8/2010 |
| JP | 2022507813 A | 1/2022 |
| JP | 2022549118 A | 11/2022 |
| JP | 2023515580 A | 4/2023 |
| WO | 1996027327 A1 | 9/1996 |
| WO | 2000038783 A1 | 7/2000 |
| WO | 2007028035 A2 | 3/2007 |
| WO | 2007109656 A2 | 9/2007 |
| WO | 2013058958 A1 | 4/2013 |
| WO | 2016199142 A1 | 12/2016 |
| WO | 2017066121 A1 | 4/2017 |
| WO | 2017070322 A1 | 4/2017 |
| WO | 2017205565 A1 | 11/2017 |
| WO | 2018039162 A2 | 3/2018 |
| WO | 2018053467 A1 | 3/2018 |
| WO | 2020106440 A1 | 5/2020 |
| WO | 2020106862 A1 | 5/2020 |
| WO | 2020125839 A1 | 6/2020 |
| WO | 2020106440 A8 | 7/2020 |
| WO | 2020106440 A8 | 10/2020 |
| WO | 2021005146 A1 | 1/2021 |
| WO | 2021007071 A1 | 1/2021 |
| WO | 2021007210 A1 | 1/2021 |
| WO | 2021046313 A1 | 3/2021 |
| WO | 2021055146 A1 | 3/2021 |
| WO | 2021174215 A1 | 9/2021 |
| WO | 2021183487 A1 | 9/2021 |
| WO | 2021247490 A1 | 12/2021 |
| WO | 2022133501 A1 | 6/2022 |
| WO | 2021174215 A9 | 9/2022 |

OTHER PUBLICATIONS

Pellerano et al., "A mm-Wave Power-Harvesting RFID Tag in 90 nm CMOS", IEEE Journal of Solid-State Circuits, Aug. 2010, vol. 45, Issue 8, pp. 1627-1637, DOI: 10.1109/JSSC.2010.2049916.

Pozar, David M., "Microwave Engineering", John Wiley & Sons, Inc., Third Edition, 2005, Chapter 13 (Oscillators and Mixers): pp. 604-657, Chapter 14 (Introduction to Microwave Systems): pp. 658-708, 105 pgs.

Radiom et al., "Far-Field On-Chip Antennas Monolithically Integrated in a Wireless-Powered 5.8-GHz Downlink/UWB Uplink RFID Tag in 0.18-μm Standard CMOS", IEEE Journal of Solid-State Circuits, Sep. 2010, vol. 45, Issue 9, pp. 1746-1758, DOI: 10.1109/JSSC.2010.2055630.

Rahmani et al., "A 1.6mm3 Wirelessly Powered Reconfigurable FDD Radio with On-Chip Antennas Achieving 4.7 pJ/b TX and 1 pJ/b RX Energy Efficiencies for Medical Implants", Conference: 2020 IEEE Custom Integrated Circuits Conference (CICC), Apr. 2020, 4 pgs., DOI: 10.1109/CICC48029.2020.9075935.

Rahmani et al., "A Dual-Mode RF Power Harvesting System With an On-Chip Coil in 180-nm SOI CMOS for Millimeter-Sized Biomedical Implants", IEEE Transactions on Microwave Theory and Techniques, Oct. 2018, vol. 67, No. 1, pp. 414-428, DOI: 10.1109/TMTT.2018.2876239.

Rahmani et al., "A Wireless Power Receiver with an On-chip Antenna for Millimeter-size Biomedical Implants in 180 nm SOI CMOS", in 2017 IEEE MTT-S International Microwave symposium (IMS), Jun. 2017, pp. 300-303.

Rahmat-Samii et al., "Implanted antennas in medical wireless communications", Synthesis Lectures on Antennas, 2005, 1.1 pp. 1-82.

Rajavi et al., "An RF-powered FDD radio for neural microimplants", IEEE Journal of Solid-State Circuits, May 2017, vol. 52, Issue: 5, pp. 1221-1229, DOI: 10.1109/JSSC.2016.2645601.

Ramrakhyani et al., "Design and Optimization of Resonance-Based Efficient Wireless Power Delivery Systems for Biomedical Implants", IEEE Transactions on Biomedical Circuits and Systems, vol. 5, No. 1, Feb. 2011, pp. 48-63.

Randles, "Kinetics of rapid electrode reactions", Discussions of the Faraday Society, 1947, vol. 1, pp. 11-19.

Rategh et al., "Superharmonic Injection-Locked Frequency Dividers", IEEE Journal of Solid-State Circuits, Jun. 1999, vol. 34, No. 6, pp. 813-821.

Razavi, "Design of analog CMOS Integrated Circuits", McGraw-Hill Series in Electrical and Computer Engineering, 2001, 706 pgs., (presented in eight parts).

Razavi, Behzad, "RF Microelectronics", New Jersey: Prentice Hall, 1998, vol. 1, 98 pgs., Chapter 8: pp. 497-594.

Rodriguez et al, "Long-term results of electrical stimulation of the lower esophageal sphincter for the treatment of gastroesophageal reflux disease", Endoscopy, Aug. 2013, vol. 45, No. 8, pp. 595-604, DOI: 10.1055/s-0033-1344213.

Sample et al., "Analysis, Experimental Results, and Range Adaptation of Magnetically Coupled Resonators for Wireless Power Transfer", IEEE Transactions on Industrial Electronics, vol. 58, No. 2, Feb. 2011, pp. 544-554, DOI: 10.1109/TIE.2010.2046002.

Sankaragomathi et al., "A 27w subcutaneous wireless biosensing platform with optical power and data transfer", Proceedings of the IEEE 2014 Custom Integrated Circuits Conference, Sep. 15, 2014, pp. 1-4.

Sayenko et al., "Spinal segment-specific transcutaneous stimulation differentially shapes activation pattern among motor pools in humans", Journal of Applied Physiology, 2015, vol. 118, pp. 1364-1374, first published Mar. 26, 2015; doi: 10.1152/japplphysiol.01128.2014.

Shi et al., "A 10 mm3 Inductive Coupling Radio for Syringe-Implantable Smart Sensor Nodes", IEEE Journal of Solid-State Circuits, Nov. 2016, vol. 51, No. 11, pp. 2570-2583, DOI: 10.1109/JSSC.2016.2606162.

Shi et al., "A 10mm3 syringe-implantable near-field radio system on glass substrate", IEEE Int. Solid-State Circuits Conf. (ISSCC) Dig. Tech. Papers, pp. 448-449, Feb. 2016.

Silvetti et al., "Cardiac pacing in pediatric patients with congenital heart defects: transvenous or epicardial?", Europace, vol. 15, No. 9, Sep. 2013, published online Feb. 24, 2013, pp. 1280-1286. doi: 10.1093/europace/eut029.

Soontornpipit, "Design of an Implantable Antenna Feasibility Study for Continuous Glucose Monitoring", ECTI Transactions on Electrical Engineering, Electronics, and Communications, Feb. 2014, vol. 12, No. 1, pp. 44-52.

Stoopman et al., "Co-Design of a CMOS Rectifier and Small Loop Antenna for Highly Sensitive RF Energy Harvesters", IEEE Journal of Solid-State Circuits, Mar. 2014, vol. 49, Issue 3, pp. 622-634, DOI: 10.1109/JSSC.2014.2302793.

Sun et al., "A wirelessly powered injection-locked oscillator with on-chip antennas in 180nm SOI CMOS", 2016 IEEE MTT-S International Microwave Symposium (IMS), Aug. 11, 2016, pp. 1-3 [online], [retrieved on Aug. 14, 2020]. Retrieved from the Internet <URL: https://ieeexplore.ieee.org/abstract/document/7540249>, entire document.

(56) References Cited

OTHER PUBLICATIONS

Sun et al., "A Wirelessly Powered Injection-Locked Oscillator With On-Chip Antennas in 180-nm SOI CMOS for Spectroscopy Application", IEEE Sensors Letters, vol. 3, No. 7, Jul. 3, 2019, pp. 1-4 [online], [retrieved on Aug. 14, 2020]. Retrieved from the Internet <URL: https://ieeexplore.ieee.org/abstract/document/8754750>.
Tabesh et al., "A Power-Harvesting Pad-Less Millimeter-Sized Radio", IEEE Journal of Solid-State Circuits, Apr. 2015, vol. 50, Issue: 4, pp. 962-977, DOI: 10.1109/JSSC.2014.2384034.
Teh et al., "Design and analysis of UHF micropower CMOS DTMOST rectifiers", IEEE Transactions on Circuits and Systems—II: Express Briefs, Feb. 2009, vol. 56, No. 2, pp. 122-126, doi: 10.1109/TCSII.2008.2010190.
Theilmann et al., "A μW Complementary Bridge Rectifier with Near Zero Turn-on Voltage in SOS CMOS for Wireless Power Supplies", IEEE Transactions on Circuits and Systems I: Regular Papers, 2012, vol. 59, No. 9, pp. 2111-2124, DOI: 10.1109/TCSI.2012.2185293.
Tjong et al., "Permanent Leadless Cardiac Pacemaker Therapy A Comprehensive Review", Circulation, Apr. 11, 2017, vol. 135, pp. 1458-1470, DOI: 10.1161/CIRCULATIONAHA.116.025037.
Tolosa et al., "Electrochemically deposited iridium oxide reference electrode integrated with an electroenzymatic glutamate sensor on a multi-electrode array microprobe", Biosensors and Bioelectronics, 2013, vol. 42, pp. available online Nov. 6, 2012, pp. 256-260, http://dx.doi.org/10.1016/jbios.2012.10.061.
Van Dongen et al., "Does a coupling capacitor enhance the charge balance during neural stimulation? An empirical study", Medical & Biological Engineering and Computing, 2016, vol. 54, pp. 93-101, published online May 29, 2015, DOI 10.1007/s11517-015-1312-9.
Van Rees et al., "Implantation-related complications of implantable cardioverter-defibrillators and cardiac resynchronization therapy devices: a systematic review of randomized clinical trials", Journal of the American College of Cardiology, Aug. 30, 2011, vol. 58, Issue 10, pp. 995-1000, https://doi.org/10.1016/j.jacc.2011.06.007.
Wan et al., "Analysis and design of a thermoelectric energy harvesting system with reconfigurable array of thermoelectric generators for IoT applications", IEEE Transactions on Circuits and Systems I: Regular Papers, Sep. 2017, vol. 64, No. 9, pp. 2346-2358, DOI: 10.1109/TCSI.2017.2708763.
Weber et al., "A Miniaturized Single-Transducer Implantable Pressure Sensor With Time-Multiplexed Ultrasonic Data and Power Links", IEEE Journal of Solid-State Circuits, Apr. 2018, vol. 53, No. 4, pp. 1089-1101, DOI: 10.1109/JSSC.2017.2782086.
Weber et al., "Functional electrical stimulation using microstimulators to correct foot drop: a case study1", Canadian Journal of Physiology and Pharmacology, 2004, vol. 82, No. 8-9, first published Oct. 19, 2004, pp. 784-792, doi: 10.1139/Y04-078.
Xie et al., "Wireless power transfer and applications to sensor networks", IEEE Wireless Communications, Aug. 2013, vol. 20, Issue: 4, pp. 140-145, DOI: 10.1109/MWC.2013.6590061.
Xu et al., "A fully implantable stimulator with wireless power and data transmission for experimental investigation of epidural spinal cord stimulation", IEEE Transactions on Neural Systems and Rehabilitation Engineering, 2015, vol. 23, No. 4, pp. 683-692, DOI:10.1109/TNSRE.2015.2396574.
Yadav et al., "Low Voltage Low Power Sub-threshold Operational Amplifier in 180nm CMOS", 2017 IEEE Third International Conference on Sensing signal Processing and Security (ICSSS), 2017, 4 pgs.
Yi et al., "Analysis and design strategy of UHF micro-power CMOS rectifiers for micro-sensor and RFID applications", IEEE Transactions on Circuits and Systems I: Regular Papers, Jan. 15, 2007, vol. 54, Issue 1, pp. 153-166, DOI: 10.1109/TCSI.2006.887974.
Yu et al., "Cardiac resynchronization therapy: state of the art 2013", European Heart Journal, vol. 34, Issue 19, May 14, 2013, online published Jan. 25, 2013, pp. 1396-1403, https://doi.org/10.1093/eurheartj/ehs454.
Yvanoff et al., "A Feasibility Study of Tissue Characterization Using Implanted LC Sensors", IEEE Transactions on Antennas and Propagation, Apr. 2009, vol. 57, Issue 4, pp. 885-893, DOI: 10.1109/TAP.2009.2016073.
Zargham et al., "Fully Integrated On-Chip Coil in 0.13 μm CMOS for Wireless Power Transfer Through Biological Media", IEEE Transactions on Biomedical Circuits and Systems, Apr. 2015, vol. 9, Issue 2, pp. 259-271, DOI: 10.1109/TBCAS.2014.2328318.
Zhang et al., "A 23 μA RF-powered transmitter for biomedical applications", 2011 IEEE Radio Frequency Integrated Circuits Symposium, 4 pgs., DOI: 10.1109/RFIC.2011.5940711.
Zhang et al., "A Miniature Mode Reconfigurable Inductorless IR-UWB Transmitter—Receiver for Wireless Short-Range Communication and Vital-Sign Sensing", IEEE Journal of Emerging and Selected Topics in Circuits and Systems, vol. 8, No. 2, Jun. 2018, pp. 294-305.
Balanis, Constantine A., "Antenna Theory: Analysis and Design", John Wiley & Sons, 2016, 1095 pgs. (presented in nine parts).
Bereuter et al., "Hot Topic in Cardiac Devices—Leadless cardiac dual-chamber pacing", Europace Abstracts Supplement, 2018, 1 pg. doi:10.1093/europace/euy015.
Bereuter et al., "Leadless Dual-Chamber Pacing, A Novel Communication Method for Wireless Pacemaker Synchronization", JACC: Basic to Translational Service, Dec. 2018, vol. 3, No. 6, pp. 813-823, https://doi.org/10.1016/j.jacbts.2018.07.009.
Biederman et al., "A Fully-Integrated, Miniaturized (0.125 mm$^2$) 10.5 μW Wireless Neural Sensor", IEEE Journal of Solid-State Circuits, vol. 48, No. 4, Mar. 22, 2013, pp. 960-970, DOI: 10.1109/JSSC.2013.2238994.
Bigio et al., "Microwave absorption spectroscopy of DNA", Biopolymers, Jan. 1993, vol. 33, Issue 1, pp. 147-150, https://doi.org/10.1002/bip.360330114.
Bourdel et al., "A 9-pJ/Pulse 1.42-Vpp OOK CMOS UWB Pulse Generator for the 3.1—10.6-GHz FCC Band", IEEE Transactions on Microwave Theory and Techniques, vol. 58, No. 1, Jan. 2010, pp. 1-9.
Brown et al., "An Ultra-Low-Power 9.8 GHz Crystal-Less UWB Transceiver with Digital Baseband Integrated in 0.18 μm BiCMOS", IEEE International Solid-State Circuits Conference, 2013, pp. 442-443.
Carlson et al., "A 20 mV Input Boost Converter with Efficient Digital Control for Thermoelectric Energy Harvesting", IEEE Journal of Solid-State Circuits, vol. 45, Issue 4, Apr. 2010, pp. 741-750.
Chae et al., "A 128-Channel 6 mW Wireless Neural Recording IC With Spike Feature Extraction and UWB Transmitter", IEEE Transactions on Neural Systems and Rehabilitation Engineering, vol. 17, No. 4, Aug. 2009, pp. 312-321.
Chang et al., "27.7 A 30.5mm3 fully packaged implantable device with duplex ultrasonic data and power links achieving 95kb/s with <10-4 BER at 8.5cm depth", IEEE International Solid-State Circuits Conference (ISSCC), Feb. 5-9, 2017, pp. 460-461, DOI: 10.1109/ISSCC.2017.7870460.
Charthad et al., "A mm-sized implantable medical device (IMD) with ultrasonic power transfer and a hybrid bi-directional data link", IEEE Journal of Solid-State Circuits, vol. 50, Issue 8, Aug. 2015, pp. 1741-1753, DOI: 10.1109/JSSC.2015.2427336.
Charthad et al., "A mm-Sized Wireless Implantable Device for Electrical Stimulation of Peripheral Nerves", IEEE Transactions on Biomedical Circuits and Systems, vol. 12, No. 2, Apr. 2018, pp. 257-270, doi: 10.1109/TBCAS.2018.2799623.
Charthad et al., "System-Level Analysis of Far-Field Radio Frequency Power Delivery for mm-Sized Sensor Nodes", IEEE Transactions on Circuits and Systems I: Regular Papers, Feb. 3, 2016, vol. 63, No. 2, pp. 300-311, DOI: 10.1109/TCSI.2015.2512720.
Chen et al., "3D Radar Imaging based on a Synthetic Array of 30GHz Impulse Radiators with On-Chip Antennas in 130nm SiGe BiCMOS", IEEE Transactions on Microwave Theory and Techniques, Nov. 2017, vol. 65, No. 22, pp. 4373-4384.
Chen et al., "Multiple leadless pacemakers implanted in the right ventricle of swine", Europace, 2016, vol. 18, 1748-1752, published online Jan. 31, 2016, doi:10.1093/europace/euv418.
Cheng, "Field and wave electromagnetics", Pearson Education India, 1989, 720 pgs., (presented in three parts).

(56) References Cited

OTHER PUBLICATIONS

Chinitz et al., "Accelerometer-based atrioventricular synchronous pacing with a ventricular leadless pacemaker: Results from the Micra atrioventricular feasibility studies", Heart Rhythm, 2018, vol. 15, pp. 1363-1371, https://doi.org/10.1016/j.hrthm.2018.05.004.

Cogan et al., "Neural stimulation and recording electrodes", Annual Review of Biomedical Engineering, 2008, vol. 10, pp. 275-309, first published online Apr. 22, 2008, doi: 10.1146/annurev.bioeng.10.061807.160518.

Dagan et al., "A low-power low-cost 24 ghz rfid tag with a c-flash based embedded memory", IEEE Journal of Solid-State Circuits, Sep. 2014, vol. 49, No. 9, pp. 1942-1957, DOI: 10.1109/JSSC.2014.2323352.

Dagdeviren et al., "Conformal piezoelectric energy harvesting and storage from motions of the heart, lung, and diaphragm", PNAS, vol. 111, No. 5, Feb. 4, 2014, published online Jan. 21, 2014, pp. 1927-1932, doi: 10.1073/pnas.1317233111.

De Roover et al., "A fully integrated wireless power supply for pinless active RFID-devices in 130nm CMOS", 2007 IEEE Asian Solid-State Circuits Conference, Nov. 12-14, 2007, pp. 123-126, DOI: 10.1109/ASSCC.2007.4425747.

Deer et al., "The Appropriate Use of Neurostimulation: Avoidance and Treatment of Complications of Neurostimulation Therapies for the Treatment of Chronic Pain", Neuromodulation: Technology at the Neural Interface, Aug. 12, 2014. vol. 17, No. 6, pp. 571-598, DOI: 10.1111/ner.12206.

Derksen et al., "Tissue Discontinuities Affect Conduction Velocity Restitution", Circulation, Aug. 19, 2003, vol. 108, Issue 7, pp. 882-888, https://doi.org/10.1161/01.CIR.0000081766.16185.28.

Dickson, "On-chip high-voltage generation in MNOS integrated circuits using an improved voltage multiplier technique", IEEE Journal of Solid-State Circuits, 1976, vol. 11, No. 3, pp. 374-378, http://dx.doi.org/10.1109/JSSC.1976.1050739.

Dorta-Quinones et al., "A Wireless FSCV Monitoring IC With Analog Background Subtraction and UWB Telemetry", IEEE Transactions on Biomedical Circuits and Systems, vol. 10, No. 2, Apr. 2016, 36 pgs.

Dosdall et al., "Mechanisms of defibrillation", Annual Review of Biomedical Engineering, vol. 12, Aug. 15, 2010, first published as a Review in Advance May 5, 2010, pp. 233-258, https://doi.org/10.1146/annurev-bioeng-070909-105305.

Eldeeb et al., "A 0.4-V Miniature CMOS Current Mode Instrumentation Amplifier", IEEE Transactions on Circuits and Systems—II Express Briefs, Mar. 2018, Vo. 65, No. 3, pp. 261-265, DOI: 10.1109/TCSII.2017.2685589.

FCC, "First Report and Order 02-48", Federal Communication Commission (FCC), Feb. 2002, 118 pgs., (presented in two parts).

Fenton et al., "Termination of Atrial Fibrillation Using Pulsed Low-Energy Far-Field Stimulation", Circulation, Aug. 11, 2009, vol. 120, Issue 6, 467-476, first published Jul. 27, 2009, https://doi.org/10.1161/CIRCULATIONAHA.108.825091.

Gao et al., "A 71GHz RF Energy Harvesting Tag with 8% Efficiency for Wireless Temperature Sensors in 65nm CMOS", IEEE Radio Frequency Integrated Circuits Symposium (RFIC), Jun. 2013, pp. 403-406, DOI: 10.1109/RFIC.2013.6569616.

Gilbert, "Impedance matching with lossy components", IEEE Transactions on Circuits and Systems, Feb. 1975, vol. 22, Issue: 2, pp. 96-100, DOI: 10.1109/TCS.1975.1084016.

Grenier et al., "Recent advances in microwave-based dielectric spectroscopy at the cellular level for cancer investigations", IEEE Transactions on Microwave Theory and Techniques, Apr. 11, 2013, vol. 61, No. 5, pp. 2023-2030, doi:10.1109/TMTT.2013.2255885.

Guler et al., "Power Management in Wireless Power-Sipping Devices: A Survey", IEEE Circuits and Systems Magazine, Nov. 20, 2017, pp. 64-82, DOI: 10.1109/MCAS .2017.2757090.

Gunturi et al., "A 250-Mb/s Data Rate IR-UWB Transmitter Using Current-Reused Technique", IEEE Transactions on Microwave Theory and Techniques, vol. 65, No. 11, Nov. 2017, pp. 4255-4265, DOI:10.1109/TMTT.2017.2695189.

Hannan et al., "Energy harvesting for the implantable biomedical devices: issues and challenges", BioMedical Engineering OnLine, 2014, vol. 13, No. 79, 23 pgs., https://doi.org/10.1186/1475-925X-13-79.

International Preliminary Report on Patentability for International Application PCT/US2019/059657, Report dated May 25, 2021, dated Jun. 3, 2021, 8 Pgs.

International Preliminary Report on Patentability for International Application PCT/US2019/062443, Report dated May 25, 2021, dated Jun. 3, 2021, 7 Pgs.

International Preliminary Report on Patentability for International Application PCT/US2020/040283, Report dated Jan. 11, 2022, dated Jan. 20, 2022, 07 Pgs.

International Preliminary Report on Patentability for International Application PCT/US2020/041007, Report dated Jan. 11, 2022, dated Jan. 20, 2022, 06 Pgs.

International Preliminary Report on Patentability for International Application PCT/US2020/048001, Report dated Mar. 15, 2022, dated Mar. 31, 2022, 6 Pgs.

International Search Report and Written Opinion for Application PCT/US2021/35132, completed Aug. 2, 2021, dated Oct. 4, 2021, 10 pgs.

International Search Report and Written Opinion for International Application No. PCT/US2019/059657, Search completed Dec. 31, 2019, dated Jan. 21, 2020, 12 Pgs.

International Search Report and Written Opinion for International Application No. PCT/US2019/062443, Search completed Jan. 15, 2020, dated Jan. 29, 2020, 15 Pgs.

International Search Report and Written Opinion for International Application No. PCT/US2020/040283, Search completed Aug. 17, 2020, dated Sep. 28, 2020, 17 Pgs.

International Search Report and Written Opinion for International Application No. PCT/US2020/048001, Search completed Oct. 17, 2020, dated Nov. 20, 2020, 12 Pgs.

International Search Report and Written Opinion for International Application No. PCT/US2021/020343, Search completed Jun. 2, 2021, dated Jun. 22, 2021, 13 Pgs.

International Search Report and Written Opinion for International Application No. PCT/US2021/073036, Search completed Apr. 14, 2022, dated May 3, 2022, 18 Pgs.

International Search Report and Written Opinion for International Application PCT/US2017/0047901, filed Aug. 22. 2017, 13 pgs.

International Search Report and Written Opinion for International Application PCT/US2017/052163, filed Sep. 19, 2017, 13 pgs.

International Search Report and Written Opinion for International Application PCT/US2020/049349, dated Nov. 24, 2020, 7 pgs.

International Search Report and Written Opinion for International Application PCT/US2021/21467, dated Jun. 3, 2021, 9 pgs.

International Search Report Search Report for International Application No. PCT/US2020/041007; Search completed Aug. 29, 2020, dated Oct. 2, 2020,13 pgs.

Abiri et al., "Inductively powered wireless pacing via a miniature pacemaker and remote stimulation control system", Science Reports, vol. 7, No. 6180, Jul. 21, 2017. pp. 1-10, doi: 10.1038/s41598-017-06493-5.

Agarwal et al., "A 4 µW, ADPLL-Based Implantable Amperometric Biosensor in 65nm CMOS", 2017 Symposium on VLSI Circuits, Kyoto, Japan, 2017, pp. C108-C109. doi: 10.23919/VLSIC.2017.8008566.

Ahn et al., "Optimal Design of Wireless Power Transmission Links for Millimeter-Sized Biomedical Implants", IEEE Transactions on Biomedical Circuits and Systems, Jan. 20, 2015, vol. 10, Issue 1, pp. 125-137, DOI: 10.1109/TBCAS.2014.2370794.

Arfin et al., "An energy-efficient, adiabatic electrode stimulator with inductive energy recycling and feedback current regulation", IEEE Transactions on Biomedical Circuits and Systems, Feb. 2012, vol. 6, Issue 1, pp. 1-14, first published Oct. 6, 2011, DOI: 10.1109/TBCAS.2011.2166072.

Atzori et al., "The Internet of Things: A survey", Computer Networks, Oct. 2010, vol. 54, Issue 15, pp. 2787-2805, https://doi.org/10.1016/j.comnet.2010.05.010.

(56) References Cited

OTHER PUBLICATIONS

Bahrami et al., "Flexible, polarization-diverse UWB antennas for implantable neural recording systems", IEEE Transactions on Biomedical Circuits and Systems, vol. 10, No. 1, Feb. 2016, pp. 38-48.
Hehn et al., "A Fully Autonomous Integrated Interface Circuit for Piezoelectric Harvesters", IEEE Journal of Solid-State Circuits, Sep. 2012, vol. 47, Issue 9, pp. 2185-2198, DOI: 10.1109/JSSC.2012.2200530.
Higgins et al., "Advances in Pacing Therapy: Examining the Potential Impact of Leadless Pacing Therapy", Journal of Innovations in Cardiac Rhythm Management, Nov. 2014, vol. 5, pp. 1825-1833, DOI: 10.19102/icrm.2014.051106.
Ho et al., "Wireless power transfer to deep-tissue microimplants", PNAS, vol. 111, No. 22, Jun. 3, 2014, first published May 19, 2014, pp. 7974-7979, https://doi.org/10.1073/pnas.1403002111.
Huang et al., "A simple subthreshold cmos voltage reference circuit with channel-length modulation compensation", IEEE Transactions on Circuits and Systems—II: Express Briefs, Sep. 2006, vol. 53, No. 9, pp. 882-885, DOI: 10.1109/TCSII.2006.881813.
Huang et al., "Materials and designs for wireless epidermal sensors of hydration and strain", Advanced Functional Materials, Jul. 2, 2014, vol. 24, Issue 25, pp. 3846-3854, first published Mar. 2, 2014, doi: 10.1002/adfm.201303886.
Huang et al., "Neurostimulation Strategy for Stress Urinary Incontinence", IEEE Transactions on Neural Systems and Rehabilitation Engineering, Jul. 2017, vol. 25, No. 7, pp. 1068-1078, first published Mar. 7, 2017, doi: 10.1109/TNSRE.2017.2679077.
Jawad et al., "Opportunities and Challenges for Near-Field Wireless Power Transfer: A Review", Energies, vol. 10, No. 1022, Jul. 18, 2017, 28 pgs., doi:10.3390/en10071022.
Jeon et al., "A 143nW Glucose-Monitoring Smart Contact Lens IC with a Dual-Mode Transmitter for Wireless-Powered Backscattering and RF-Radiated Transmission Using a Single Loop Antenna", Symposium on VLSI Circuits, Jun. 9-14, 2019, pp. C294-C295, DOI: 10.23919/VLSIC.2019.8777984.
Jia et al., "A mm-sized free-floating wirelessly powered implantable optical stimulating system-on-a-chip", 2018 IEEE International Solid—State Circuits Conference—(ISSCC), Feb. 11-15, 2018, San Francisco, CA, pp. 468-470, DOI: 10.1109/ISSCC.2018.8310387.
Jiang et al., "A Sub-1 µW Multiparameter Injectable BioMote for Continuous Alcohol Monitoring", IEEE Custom Integrated Circuits Conference (CICC), 2018, pp. 1-4.
Johnson et al., "StimDust: A 6.5 mm3, wireless ultrasonic peripheral nerve stimulator with 82% peak chip efficiency", UC BerkeleyRetrieved from https://escholarship.org/uc/item/8px811qc, published May 5, 2019, 5 pgs., http://dx.doi.org/10.1109/CICC.2018.8357047.
Kang et al., "A 1.7x4.1x2 mm3 Fully Integrated pH Sensor for Implantable Applications Using Differential Sensing and Drift-Compensation", 2019 Symposium on VLSI Circuits Digest of Technical Papers, C25-1, pp. C310- C311.
Kang et al., "Design and Optimization of Area-Constrained Wirelessly Powered CMOS UWB SoC for localization applications", IEEE Transactions on Microwave Theory and Techniques, Apr. 2016, vol. 64, No. 4, pp. 1042-1054, DOI: 10.1109/TMTT.2016.2536663.
Karthaus et al., "Fully Integrated Passive UHF RFID Transponder IC With 16.7-µW Minimum RF Input Power", IEEE Journal of Solid State Circuits, Oct. 2003, vol. 38, No. 10, pp. 1602-1608, DOI: 10.1109/JSSC.2003.817249.
Kelly et al., "A power-efficient neural tissue stimulator with energy recovery", IEEE Transactions on Biomedical Circuits and Systems, Feb. 2011, vol. 5, Issue 1, pp. 20-29, first published Jan. 24, 2011, DOI: 10.1109/TBCAS.2010.2076384.
Kennedy et al., "High intensity focused ultrasound: surgery of the future?", British Journal of Radiology, Sep. 2003, vol. 76, No. 909, pp. 590-599, doi: 10.1259/bjr/17150274.
Kim et al., "A 144-MHz Fully Integrated Resonant Regulating Rectifier with Hybrid Pulse Modulation for mm-Sized Implants", IEEE Journal of Solid-State Circuits, Nov. 2017, vol. 52, Issue 11, pp. 3043-3055, DOI: 10.1109/JSSC.2017.2734901.
Kim et al., "Design of miniaturized wireless power receivers for mm-sized implants", 2017 IEEE Custom Integrated Circuits Conference (CICC), Apr. 30-May 30, 2017, 8 pgs., DOI: 10.1109/CICC.2017.7993703.
Kim et al., "Wireless power transfer to a cardiac implant", Applied Physics Letters, vol. 101, 2012, pp. 073701-1-073701-4; doi: 10.1063/1.4745600.
Kocer et al., "A new transponder architecture with on-chip ADC for long-range telemetry applications", IEEE Journal of Solid-State Circuits, vol. 41, No. 5, Apr. 24, 2006, pp. 1142-1148 [online], [retrieved on Aug. 14, 2020]. Retrieved from the Internet <URL: https://www.mpflynngroup.com/uploads/7/3/4/9/73490609/01624404.pdf>, entire document, especially: fig. 1, p. 1, col. 2, para. 3; p. 2, col. 2, para 2.
Kotani et al., "High-Efficiency Differential-Drive CMOS Rectifier for UHF RFIDs", IEEE Journal of Solid-State Circuits, Nov. 2009, vol. 44, Issue 11, pp. 3011-3018, DOI:10.1109/JSSC.2009.2028955.
Kulkarni et al., "A 750 Mb/s, 12 pJ/b, 6-to-10 GHz CMOS IR-UWB Transmitter with Embedded On-Chip Antenna", IEEE Journal of Solid-State Circuits, vol. 44, No. 2, Feb. 2009, pp. 394-403, DOI: 10.1109/JSSC.2008.2011034.
Kuo et al., "Near-field power transfer and backscattering communication to miniature RFID tag in 65 nm CMOS technology", 2016 IEEE MTT-S International Microwave Symposium (IMS), May 22-27, 2016, 4 pgs., DOI: 10.1109/MWSYM.2016.7540221.
Kurs et al., "Wireless Power Transfer via Strongly Coupled Magnetic Resonances", Science, vol. 317, No. 5834, Jul. 6, 2007, published online Jun. 7, 2007, pp. 83-86, DOI: 10.1126/science.1143254.
Le et al., "Efficient Far-Field Radio Frequency Energy Harvesting for Passively Powered Sensor Networks", IEEE Journal of Solid-State Circuits, May 2008, vol. 43, No. 5, pp. 1287-1302, DOI: 10.1109/JSSC.2008.920318.
Lepock, "Cellular effects of hyperthermia: relevance to the minimum dose for thermal damage", International Journal of Hyperthermia, vol. 19, No. 3, May-Jun. 2003, pp. 252-266, DOI: 10.1080/0265673031000065042.
Li et al., "A 13.56 MHz Wireless Power Transfer System with Reconfigurable Resonant Regulating Rectifier and Wireless Power Control for Implantable Medical Devices", IEEE Journal of Solid-State Circuits, vol. 50, No. 4, Apr. 1, 2015, pp. 978-989.
Liu et al., "A 650-pJ/bit MedRadio transmitter with an FIR-embedded phase modulator for medical micro-power networks (MMNs)", IEEE Transactions on Circuits and Systems I: Regular Papers, 2013, vol. 60, No. 12, pp. 3279-3288, DOI: 10.1109/TCSI.2013.2265970.
Lo et al., "A fully integrated wireless SoC for motor function recovery after spinal cord injury", IEEE Transactions on Biomedical Circuits and Systems, Jun. 2017, vol. 11, Issue 3, pp. 497-509, first published May 23, 2017, DOI: 10.1109/TBCAS.2017.2679441.
Lo et al., "Bio-Impedance Characterization Technique with Implantable Neural Stimulator Using Biphasic Current Stimulus", Conference Proceedings of the IEEE Engineering in Medicine and Biology Society, 2014, pp. 474-477, doi: 10.1109/EMBC.2014.6943631.
Lonappan et al., "Nondestructive Measurement of Human Blood at Microwave Frequencies", Journal of Electromagnetic Waves and Applications, 2007, vol. 21, Issue 8, 1131-1139, DOI: 10.1163/156939307781749740.
Lopez-Lapena et al., "A closed-loop maximum power point tracker for subwatt photovoltaic panels", IEEE Transactions on Industrial Electronics, Mar. 2012, vol. 59, No. 3, pp. 1588-1596, DOI: 10.1109/TIE.2011.2161254.
Lu et al., "Flexible Neural Electrode Array Based-on Porous Graphene for Cortical Microstimulation and Sensing", Scientific Reports, Sep. 19, 2016, vol. 6, No. 33526, 9 pgs., DOI: 10.1038/srep33526.
Lu et al., "Ultra-flexible Piezoelectric Devices Integrated with Heart to Harvest the Biomechanical Energy", Scientific Reports, vol. 5, No. 16065, Nov. 5, 2015, 9 pgs., https://doi.org/10.1038/srep16065.
Lyu et al., "A 430-Mhz Wirelessly Powered Implantable Pulse Generator with Intensity/Rate Control and Sub-1 µA Quiescent

(56) References Cited

OTHER PUBLICATIONS

Current Consumption", IEEE Transactions on Biomedical Circuits and Systems, vol. 13, No. 1, Feb. 2019, pp. 180-190, DOI: 10.1109/TBCAS.2018.2879357.

Lyu et al., "A 915-MHz Far-Field Energy Harvester with −22-dBm Sensitivity and 3-V Output Voltage Based on Antenna-and-Rectified Codesign", IEEE Microwave and Wireless Components Letters, Aug. 2019, vol. 29, No. 8, pp. 557-559, DOI: 10.1109/LMWC.2019.2923685.

Lyu et al., "A Multi-site Heart Pacing Study Using Wirelessly Powered Leadless Pacemakers", IEEE Xplore, Year: 2018, Date: Oct. 29, 2018 (retrieved on Jan. 15, 2020).

Lyu et al., "An Energy-Efficient Wirelessly Powered Millimeter-Scale Neurostimulator Implant Based on Systematic Codesign of an Inductive Loop Antenna and a Custom Rectifier", IEEE Transactions on Biomedical Circuits and Systems, vol. 12, No. 5, Oct. 2018, pp. 1131-1143, DOI: 10.1109/TBCAS.2018.2852680.

Lyu et al., "Synchronized Biventricular Heart Pacing in a Closed-chest Porcine Model based on Wirelessly Powered Leadless Pacemakers", Scientific Reports, 10, Article No. 2067, 2020, 13 pgs.

Lyu et al., "Towards the Implementation of a Wirelessly Powered Dielectric Sensor with Digitized Output for Implantable Applications", IEEE Sensors Letters, Mar. 2019, vol. 3, No. 3, pp. 1-4, first published Jan. 30, 2019.

Mandal et al., "Low-power CMOS rectifier design for RFID applications", IEEE Transactions on Circuits and Systems I: Regular Papers, Jul. 2007, vol. 54, No. 6, pp. 1177-1188, DOI:10.1109/TCSI.2007.895229.

Meyer et al., "First in a series on the leadless pacing: Percutaneous implantable transcatheter pacemaker—background, technical aspects, and possible pitfalls", d-Journal of Cardiology Practice, Aug. 23, 2016, vol. 14, No. 20, 18 pgs.

Mirbozorgi et al., "A Single-Chip Full-Duplex High Speed Transceiver for Multi-Site Stimulating and Recording Neural Implants", IEEE Transactions on Biomedical Circuits and Systems, vol. 10, No. 3, Jun. 2016, pp. 643-653, DOI: 10.1109/TBCAS.2015.2466592.

Mirzavand et al., "High-Resolution Dielectric Sensor Based on Injection-Locked Oscillators", IEEE Sensors Journal, Jan. 1, 2018, vol. 18, Issue 1, pp. 141-148, published online published Nov. 13, 2017, DOI: 10.1109/JSEN.2017.2772923.

Montgomery et al., "Wirelessly powered, fully internal optogenetics for brain, spinal and peripheral circuits in mice", Nature Methods, 2015, vol. 12, No. 10, pp. 969-974, published online Aug. 17, 2015, DOI: 1031038/NMETH.3536.

Niemann et al., "Longevity of Implantable Pulse Generators in Bilateral Deep Brain Stimulation for Movement Disorders", Neuromodulation, vol. 21, No. 6, Aug. 2018, published online Dec. 19, 2017, pp. 597-603, doi: 10.1111/ner.12743.

Pandey et al., "A Sub-100 μW MICS/ISM Band Transmitter Based on Injection-Locking and Frequency Multiplication", IEEE Journal of Solid-State Circuits, May 2011, vol. 46, Issue 5, pp. 1049-1058, first published Apr. 5, 2011, DOI: 10.1109/JSSC.2011.2118030.

Papotto et al., "A 90nm CMOS 5mb/s crystal-less rf transceiver for rf-powered wsn nodes", 2012 IEEE International Solid-State Circuits Conference, Feb. 19-23, 2012, pp. 451-453, DOI: 10.1109/ISSCC.2012.6177087.

Extended European Search Report dated Jul. 19, 2022, issued in related European Application No. 19887763.1, 7 pgs.

Extended European Search Report for European Application No. 19887763.1, Search completed Jul. 11, 2022, dated Jul. 19, 2022, 07 Pgs.

International Preliminary Report on Patentability dated Sep. 22, 2022 issued in related International Application PCT/US2021/021467, 6 pgs.

International Preliminary Report on Patentability for International Application PCT/US2021/020343, Report dated Aug. 30, 2022, dated Sep. 9, 2022, 7 Pgs.

International Search Report and Written Opinion for International Application No. PCT/US2022/036926, Search completed Sep. 8, 2022, dated Oct. 17, 2022, 07 pgs.

Balanis, "Antenna Theory: Analysis and Design", Wiley-Interscience, 3rd Edition, Apr. 4, 2005, 1136 pgs.

Zargham et al., "Fully Integrated on-Chip Coil in 0.13 μm CMOS for Wireless Power Transfer Through Biological Media", IEEE Transactions on Biomedical Circuits and Systems, Aug. 2014, vol. 9, No. 2, 13 pgs., DOI:10.1109/TBCAS.2014.2328318.

Extended European Search Report for European Application No. 20860681.4, Search completed Jul. 26, 2023, dated Aug. 2, 2023, 7 Pgs.

International Preliminary Report on Patentability for International Application PCT/US2021/073036, Report dated Jun. 13, 2023, dated Jun. 29, 2023, 09 Pgs.

Rahmani et al., "An Integrated Battery-Less Wirelessly Powered RFID Tag with Clock Recovery and Data Transmitter for UWB Localization", Microwave, MTT-S International Symposium, Aug. 4-6, 2020, Los Angeles, CA, USA, pp. 460-463, DOI: 10.1109/IMS30576.2020.9223821.

Choi et al., "A Wirelessly Powered Microspectrometer for Neural Probe-Pin Device.", Micro+Nano Materials, Devices, and Systems, 2015, vol. 9668. SPIE, 8 pgs.

\* cited by examiner

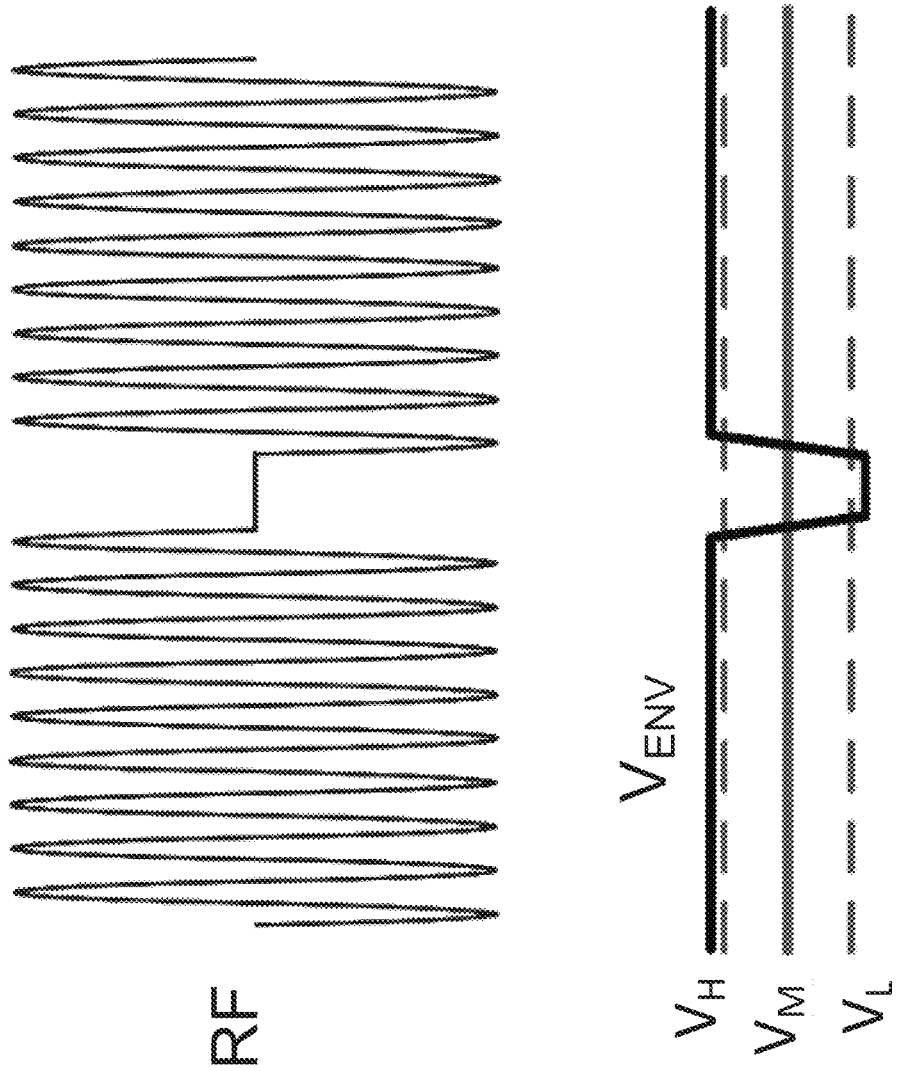

SYSTEMS AND METHODS FOR CONTROLLING WIRELESSLY POWERED LEADLESS PACEMAKERS

CROSS-REFERENCE TO RELATED APPLICATIONS

The current application is a national stage application of PCT Application No. PCT/US2019/062443 entitled "Systems and Methods for Controlling Wirelessly Powered Leadless Pacemakers" filed Nov. 20, 2019, which claims the benefit of and priority under 35 U.S.C. § 119(e) to U.S. Provisional Patent Application No. 62/769,984 entitled "Synchronized Biventricular Heart Pacing using Wirelessly powered, leadless pacemakers" filed Nov. 20, 2018, and U.S. Provisional Patent Application No. 62/845,619 entitled "Synchronized Biventricular Heart Pacing using Wirelessly powered, leadless pacemakers" filed May 9, 2019. The disclosures of PCT Application No. PCT/US2019/062443 and U.S. Provisional Patent Application Nos. 62/769,984 and 62/845,619 are hereby incorporated by reference in its entirety for all purposes.

FEDERAL FUNDING

This invention was made with government support under Grant Number 1533688 awarded by the National Science Foundation. The government has certain rights in the invention.

FIELD OF THE INVENTION

The present invention relates to systems and methods for heart pacing using wirelessly powered, leadless pacemakers, namely powering and control of one or more wirelessly powered, leadless pacemakers.

BACKGROUND

The heart is a critical muscle in humans and many other animals that is responsible for circulating blood through the circulatory system. The human heart is made up of four chambers, two upper atria, and two lower ventricles, organized into a left and right pairing of an atrium and a ventricle. In a healthy heart, the chambers contract and relax in a synchronized fashion, referred to as a "beat," in order to force blood through the network of veins and arteries.

Irregular heartbeats can pose a health risk, and in some cases regular beating can be restored via electrical stimulation. Implantable devices called "pacemakers" are devices which can stimulate the muscle tissue, causing it to contract. By carefully and regularly applying stimulation as needed, normal heart rhythm can be restored. Leadless pacemakers are a specific class of pacemaker which can be made considerably smaller than a standard pacemaker which does not have any external wires ("leads").

Wireless power transfer refers to the transfer of electrical energy without wires as a physical channel. There are many different wireless power transfer systems involving both radiative and nonradiative techniques. An example of a nonradiative technique is electromagnetic induction or near-field coupling, where by power is transferred via magnetic fields by inductive coupling (resonant or non-resonant) between coils of wire or via electric fields by capacitive coupling between metal electrodes.

SUMMARY OF THE INVENTION

Systems and methods for heart stimulation in accordance with embodiments of the invention are illustrated. One embodiment includes a heart stimulation system, including a first wirelessly powered, leadless pacemaker, including a first wireless power receiver tuned to a first frequency, a first energy harvesting circuitry, a first stimulation circuitry, and a first stimulation electrode, a controller, including a first wireless power signal generator, a first wireless power transmitter tuned to the first frequency, a processor, and a memory containing a stimulation control application, where the stimulation control application directs the processor to generate a first power transfer signal using the first wireless power signal generator, and transmit the first power transfer signal using the first wireless power transmitter, wherein the first wirelessly powered, leadless pacemaker receives the first power transfer signal using the first wireless power receiver, and when receiving the first power transfer signal, the first energy harvesting circuitry stores power received via the wireless power receiver in at least one capacitor.

In another embodiment, when not receiving the first power transfer signal, the first stimulation circuitry discharges the stored power via the first stimulation electrode.

In a further embodiment, the first wireless power transmitter is a near field resonant coupling based transmitter coil; and wherein the first wireless power receiver is a near field resonant coupling based receiver coil.

In still another embodiment, the first wireless power transmitter is a far field propagating electromagnetic wave receiver antenna; and wherein the first wireless power receiver is a far field propagating electromagnetic wave transmitter antenna.

In a still further embodiment, the system further includes a second wirelessly powered, leadless pacemaker, including a second wireless power receiver tuned to a second frequency, a second energy harvesting circuitry, a second stimulation circuitry; and a second stimulation electrode, wherein the controller further includes, a second wireless power signal generator, and a second wireless power transmitter tuned to the second frequency, wherein the stimulation control application further directs the processor to generate a second power transfer signal using the second wireless power signal generator, and transmit the second power transfer signal using the second wireless power transmitter, wherein the second wirelessly powered, leadless pacemaker receives the second power transfer signal using the second wireless power receiver, when receiving the second power transfer signal, the second energy harvesting circuitry stores power received via the second wireless power receiver in at least one capacitor of the second wirelessly, powered leadless pacemaker; and when not receiving the second power transfer signal, the stimulation circuitry of the second wirelessly, powered leadless pacemaker discharges the stored electricity via the second stimulation electrode.

In yet another embodiment, the stimulation control application further directs the processor to time the transmission of the first power transfer signal and the second power transfer signal such that stimulation by the first wirelessly powered, leadless pacemaker and the second wirelessly powered, leadless pacemaker provide stimulation at a determined time relative to each other.

In a yet further embodiment, the first frequency and the second frequency are selected such that the first wireless power transmitter does not couple with the second wireless power receiver.

In another additional embodiment, the system further includes a second wirelessly powered, leadless pacemaker, including a second wireless power receiver tuned to the first frequency, a second energy harvesting circuitry, a second stimulation circuitry, and a second stimulation electrode, wherein the stimulation control application further directs the processor to modulate a portion of the first power transfer signal with a unique label associated with the second wirelessly powered, leadless pacemaker, and transmit the modulated first power transfer signal using the first wireless power transmitter, wherein the second wirelessly powered, leadless pacemaker receives the first power transfer signal using the second wireless power receiver, when receiving the first power transfer signal, the second energy harvesting circuitry stores power received via RF induction in at least one capacitor of the second wirelessly, powered leadless pacemaker, when receiving the portion of the first power transfer signal modulated with the unique label, the second wirelessly powered, leadless pacemaker discharges stored power via the second stimulation electrode, and when receiving the portion of the first power transfer signal modulated with the unique label, the first powered leadless pacemaker continues to store power.

In a further additional embodiment, the first wireless power transmitter is tunable to a second frequency.

In another embodiment again, the controller is an extracorporeal device.

In a further embodiment again, the controller is configured to be implanted subcutaneously.

In still yet another embodiment, the first wirelessly powered, leadless pacemaker stimulates a first chamber of a heart and the second wirelessly powered, leadless pacemaker stimulates the first chamber of the heart.

In a still yet further embodiment, the first wirelessly powered, leadless pacemaker stimulates a first chamber of the heart, and the second wirelessly powered, leadless pacemaker stimulates a second chamber of a heart.

In still another additional embodiment, the first wirelessly powered, leadless pacemaker stimulates a blood vessel in order to deliver an electrical stimulation to a heart.

In a still further additional embodiment, the first wirelessly powered, leadless pacemaker stimulates muscle tissue in order to deliver an electrical stimulation to a heart.

In still another embodiment again, the first wirelessly powered, leadless pacemaker stimulates a chamber of a heart, and a second wirelessly powered, leadless pacemaker stimulates a blood vessel in order to deliver an electrical stimulation to the heart.

In a still further embodiment again, the transmission of the first power transfer signal induces the first wirelessly powered, leadless pacemaker to deliver an electrical therapy to a heart in order to maintain normal heart condition; and the first wirelessly powered, leadless pacemaker is configured to sense heart activity.

In yet another additional embodiment, the first wirelessly powered, leadless pacemaker further includes a sensing circuitry, where the sensing circuitry is configured to sense heart activity.

In a yet further additional embodiment, the first wirelessly powered, leadless pacemaker further includes a transmitter circuitry configured to transmit sensed heart activity.

In yet another embodiment again, a method for stimulating a heart using wirelessly powered, leadless pacemakers, includes generating a first power transfer signal at a first frequency using a first wireless power signal generator of a controller, transmitting the first power transfer signal using a first wireless power transmitter of the controller, receiving, by a first wirelessly powered, leadless pacemaker, the first power transfer signal using a first wireless power receiver, and storing power received via the first power transfer signal in at least one capacitor of the first wirelessly powered, leadless pacemaker.

In a yet further embodiment again, when not receiving the first power transfer signal, the first wirelessly powered, leadless pacemaker discharges the stored power via a first stimulation electrode.

In another additional embodiment again, the method further includes generating a second power transfer signal at a second frequency using a second wireless power signal generator of the controller, transmitting the second power transfer signal using a second wireless power transmitter of the controller, receiving, by a second wirelessly powered, leadless pacemaker, the second power transfer signal using a first wireless power receiver, and storing power received via the second power transfer signal in at least one capacitor of the second wirelessly powered, leadless pacemaker.

In a further additional embodiment again, the method further includes modulating a portion of the first power transfer signal with a unique label associated with a second wirelessly powered, leadless pacemaker, receiving, by the second wirelessly powered, leadless pacemaker, the first power transfer signal using a second wireless power receiver, storing power received via the first power transfer signal in at least one capacitor of the second wirelessly powered, leadless pacemaker, discharging, by the second wirelessly powered, leadless pacemaker, stored power when receiving the modulated portion of the first power transfer signal, and continuing to store power, by the first wirelessly powered, leadless pacemaker, when receiving the modulated portion of the first power transfer signal.

In still yet another additional embodiment, a heart stimulation system includes a plurality of wirelessly powered, leadless pacemakers controlled by a controller where the controller triggers the plurality of wirelessly powered, leadless pacemakers to provide stimulation to a heart via a power transmission signal.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

FIG. 6B illustrates a waveform representing the voltages of nodes in the demodulator circuit in response to a given RF input signal in accordance with an embodiment of the invention.

DETAILED DESCRIPTION

Figure 1:
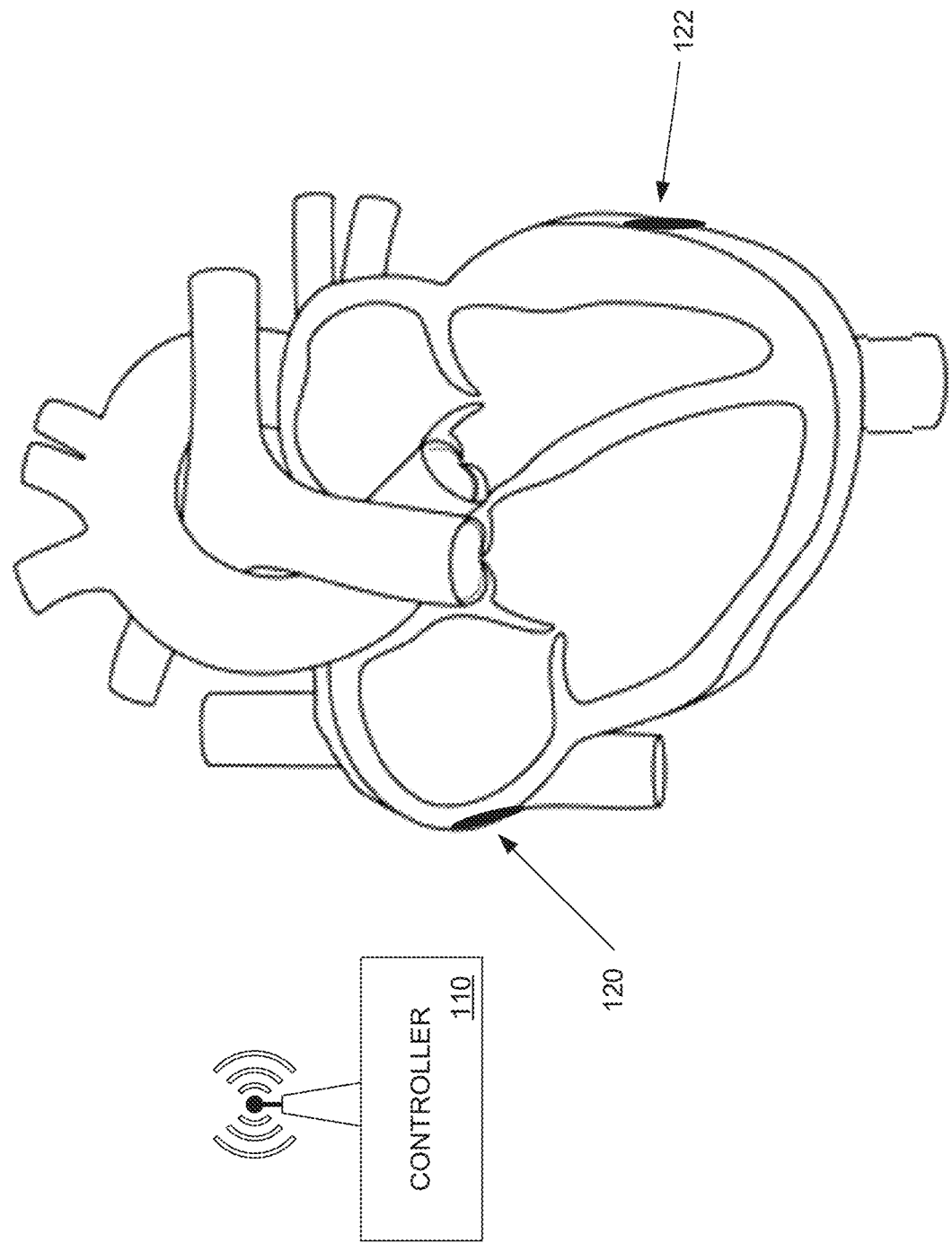
FIG. 1 illustrates a heart stimulation system in accordance with an embodiment of the invention.

Turning now to the drawings, systems and methods for heart pacing using wirelessly powered, leadless pacemakers are illustrated. Pacemakers are a critical part of many treatment regimens for those living with heart conditions. Traditional pacemakers consist of three main components: a pulse generator, one or more leads that carry the electric pulses to the heart, and an electrode at the end of each lead to deliver the stimulation. Recently, leadless pacemakers have been developed which combine a self-contained generator and electrode system which removes the need for a separate pulse generator. However, in contrast to a traditional pacemaker which uses a central pulse generator for all electrodes, systems with multiple leadless pacemakers are difficult to synchronize.

Further, it is relatively easy to replace the battery for (or entirely replace) pulse generators of traditional pacemakers which are not implanted directly into the heart, and are therefore easier to access. On the other hand, current leadless pacemakers are difficult or impossible to remove, and many run on batteries, meaning they have a limited lifespan. Some leadless pacemaker systems propose utilizing wireless power transfer systems in which power is transferred and immediately utilized to stimulate the heart. In this way, the pace timing can be directly controlled by wirelessly providing power when stimulation should occur. However, in this scheme enough power to produce the required stimulation is immediately required. Consequently, a large amount of power must be transferred wirelessly in a short period of time, which can be inefficient.

In contrast, wirelessly powered, leadless pacemakers described herein (Hereinafter referred to as "WPLPs") can easily be synchronized and efficiently powered using wireless power transfer methodologies in which necessary power for stimulation is transferred over a longer period at much lower power. Further, multiple WPLPs can be controlled as to provide stimulation at any particular moment, not necessarily at exactly the same time, depending on the therapy being administered. As a healthy heartbeat occurs between approximately 0.6-1 seconds, and as a pacemaker typically stimulates with a pulse on the order of 100-10,000 microseconds, WPLPs can receive power signals over a considerable amount of time while the heart does not need to be stimulated. In many embodiments, a controller is used to wirelessly power and synchronize one or more WPLPs implanted into a patient. In various embodiments, the controller transmits power to different WPLPs using electromagnetic and/or magnetic fields of different frequencies. However, in numerous embodiments, a single frequency electromagnetic field can be used to synchronize and/or wirelessly power multiple WPLPs. Further, in many embodiments, the signal used to produce the electromagnetic field can be modulated with control data which can be further used to control WPLPs. Any number of different WPLPs can be implanted in various locations in order to treat any number of different cardiovascular problems, such as, but not limited to, arrhythmias, heart failure, cardiomyopathy, and/or any of a number of different conditions that can benefit from stimulation and/or pacing. Indeed, in numerous embodiments, WPLPs can be implanted so as to stimulate locations normally stimulated using conventional pacemakers in order provide therapy for heart conditions. Many such pacemaker stimulation configurations are known in the art. Example treatments using conventional pacemakers which can be replicated using WPLPs are discussed in such texts as: Josephson, Mark E. *Clinical cardiac electrophysiology: techniques and interpretations*. Lippincott Williams & Wilkins, 2008; Topol, Eric J., and Paul S. Teirstein. *SPEC-Textbook of Interventional Cardiology, 12-Month Access, eBook*. Elsevier Health Sciences, 2015; and Ellenbogen, Kenneth A., Bruce L. Wilkoff, G. Neal Kay, Chu Pak Lau, and Angelo Auricchio. *Clinical Cardiac Pacing, Defibrillation and Resynchronization Therapy E-Book*. Elsevier Health Sciences, 2016, the disclosures of which are hereby incorporated by reference in their entirety. However, usage of WPLPs is not restricted to known configurations, and many implantation positions may be more viable using WPLPs. WPLP systems are described in further detail below.

WPLP Systems

WPLP systems, also referred to as "heart stimulation systems," can involve any number of individual WPLPs, which in turn are controlled via a controller. In many embodiments, the controller is implanted into the patient, but may be implemented as an external device. WPLPs can be implanted into or onto to the heart of a patient in order to provide heart pacing stimulation. The location of WPLPs can be determined based on the need of the patient and their particular condition(s). in numerous embodiments, controllers can produce radio frequency (RF) magnetic fields in order to inductively Turning now to FIG. 1, a WPLP system in accordance with an embodiment of the invention is illustrated. WPLP system 100 includes a controller 110, a first WPLP 120 implanted into the right atrium, and a second WPLP 122 implanted into the left ventricle. In many embodiments, WPLPs can be implanted in different chamber configurations as appropriate to the patient's condition. More than one WPLP can be implanted into the same chamber. Indeed, any number of WPLPs including a single WPLP can be used in a WPLP system.

WPLPs can receive power from controllers. A single controller can be used to provide power and/or control multiple WPLPs. In some embodiments, multiple controllers responsible for particular WPLPs are used. In many embodiments, the power signal generated by a controller dictates the stimulation provided by the receiving WPLP via pulse width control. That is, when the WPLP is receiving the power signal, the WPLP uses the power to charge a storage medium. When the WPLP is not receiving a power signal, the WPLP discharges the power to stimulate the heart. Due to the long time between beats, a low power signal can be used to charge the storage medium. This is opposed to the standard methodology for wirelessly powering leadless pacemakers where power received is immediately used to stimulate the heart. Controllers for generating low power signals are discussed in further detail below.

WPLP Controllers

Controllers can be used to power and/or synchronize WPLPs. In numerous embodiments, the controller is an implanted device. However in various embodiments, the controller is an external device. Indeed, controllers can be implemented using any hardware platform capable of wirelessly transmitting power to WPLPs. In many embodiments, controllers are further capable of modulating signals used to generate power transfer magnetic fields with control information, which can be used to control multiple WPLPs using a single frequency field.

Figure 2:
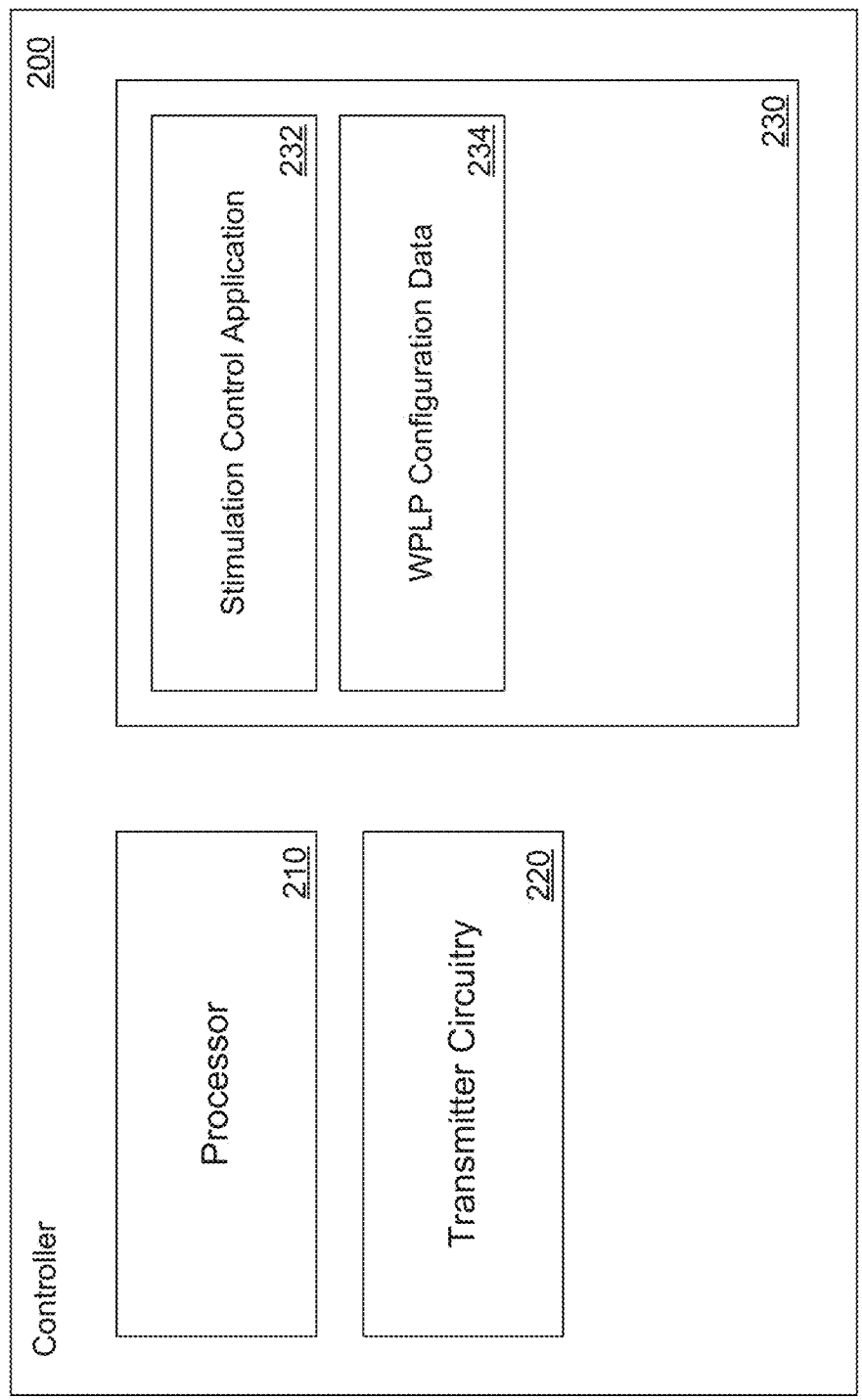
FIG. 2 is a high level block diagram for a controller in accordance with an embodiment of the invention.

Turning now to FIG. 2, a block diagram for a WPLP control in accordance with an embodiment of the invention is illustrated. Controller 200 includes a processor 210. Processors can be any logic circuitry such as, but not limited to, central processing units, graphics processing units, field-programmable gate-arrays (FPGAs), application-specific integrated circuits (ASICs), and/or any other logic circuit capable of implementing instructions as appropriate to the requirements of specific applications of a given embodiment the invention.

The controller 200 further includes a transmitter circuitry 220. The transmitter circuitry can include one or more transmission components capable of generating and/or transmitting power transfer signals, such as, but not limited to transmission coils, RF signal generators, antennas, and/or any other transmission component as appropriate to the requirements of specific applications of a given embodiment the invention. In some embodiments, signal generators can generate more than one signal frequency. In a variety of embodiments, multiple signal generators are used. In numerous embodiments, the transmitter circuitry is capable of powering WPLPs via inductive power transfer. In many embodiments, the inductive power transfer is achieved using radio-frequency induction, whereby an RF signal is passed through a coil in order to induce a radio-frequency magnetic field. Power can be received by a receiver coil resonantly coupled to the transmitter coil. Transmitter and receiver coils can be actively tuned to particular resonant frequencies, or constructed such that they only respond to a predetermined frequency or set of frequencies. In various embodiments, controllers include one or more transmitter coils that are resonantly coupled to particular WPLP receiver coils.

Controller 200 further incudes a memory 230. Memory can be implemented using a nonvolatile memory storage medium and/or a volatile memory storage medium. The memory 230 contains a stimulation control application 232. In many embodiments, the stimulation control application directs the processor to generate control information and modulate the RF signal used to drive the transmitter coil with the control information. Control information and control schemes are discussed further in a below section.

The memory 230 further contains WPLP configuration data 234. The WPLP configuration data can include any information regarding implanted WPLPs in the system, including, but not limited to, WPLP labels, WPLP locations, WPLP serial numbers, encryption information for encrypting commands, stimulation profiles, and/or any other data regarding WPLPs or their operation as appropriate to the requirements of specific applications of a given embodiment the invention. Configuration data can be used to direct the modulation of the RF signal, which RF signal frequencies are generated, what stimulation patterns should be employed, and/or any other configuration as appropriate to the requirements of specific applications of embodiments of the invention.

While a particular controller is illustrated with respect to FIG. 2, any number of different architectures can be utilized. For example, while the embodiment illustrated in FIG. 2 utilizes a software defined encoder, a hardware encoder can be utilized. Indeed, in many embodiments, the controller does not contain memory and the controller includes specialized circuitry to generate the modulated signal. In various embodiments, controllers include receivers which can receive signals from WPLPs describing sensed biological activities recorded by WPLPs. In some embodiments, the wireless power transmitter can act as a receiver, and/or separate receiver circuitry can be included. Indeed, any number of different implementations can be utilized without departing from the scope or sprit of the invention. WPLP circuitries capable of control using controllers are discussed below.

WPLP Circuitries

WPLPs can store power in a storage medium between heart beats, and discharge stored power to regulate a heartbeat. In many embodiments, the WPLP receives power from a controller via RF induction at a particular frequency. The WPLP in turn can have a receiver that is tuned to the particular frequency. In this way, stray signals are unlikely to impact functionality. Further, depending on the control scheme of the system, WPLPs can be selectively controlled via separate RF frequency magnetic fields (a "frequency division" scheme). Control schemes are discussed in a below section. In numerous embodiments, the WPLP is made of and/or encapsulated in a material that makes the circuitry safe to implant into an organism.

Figure 3:
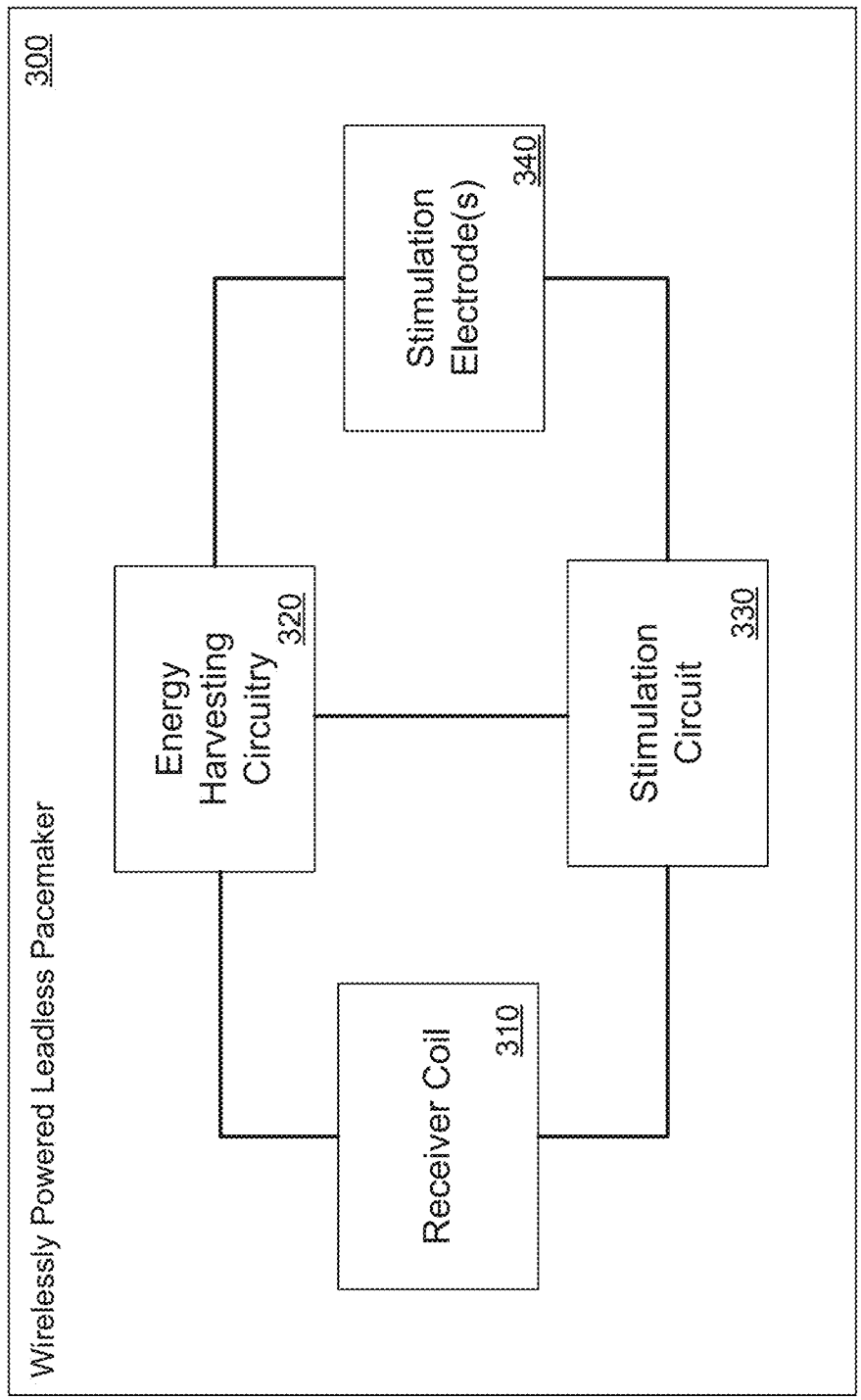
FIG. 3 is a high level block diagram for a wirelessly powered, leadless pacemaker in accordance with an embodiment of the invention.

Turning now to FIG. 3, a high level diagram of a WPLP in accordance with an embodiment of the invention is illustrated. WPLP 300 includes a wireless power receiver 310. In many embodiments, the wireless power receiver is a receiver coil, an antenna for receiving electromagnetic signals, and/or any other circuit capable of harvesting power from wireless power transmission sources as appropriate to the requirements of specific applications of embodiments of the invention. The wireless power receiver 310 sends power to energy harvesting circuitry 320. In many embodiments, the energy harvesting circuitry can rectify alternating current into direct current, and/or charge one or more electrical storage media in order to store power. In many embodiments, the electrical storage media is one or more capacitors, however any number of electrical storage media, including, but not limited to, batteries, can be used as appropriate to the requirements of specific applications of embodiments of the invention. A stimulation circuit 330 provides power to one or more stimulation electrodes 340. In numerous embodiments, the stimulation circuit is capable of recovering control information encoded in the current and controlling stimulation in accordance with the control information. In various embodiments, WPLPs include sensing circuitry which can be used to sense and/or monitor biological activity, including, but not limited to, heartbeats, temperature, blood flow, motion, and/or any other sensible property as appropriate to the requirements of specific applications of embodiments of the invention. Sensed activity can be transmitted to controllers via the wireless power receiver and/or a separate transmitter circuit.

Figure 4:
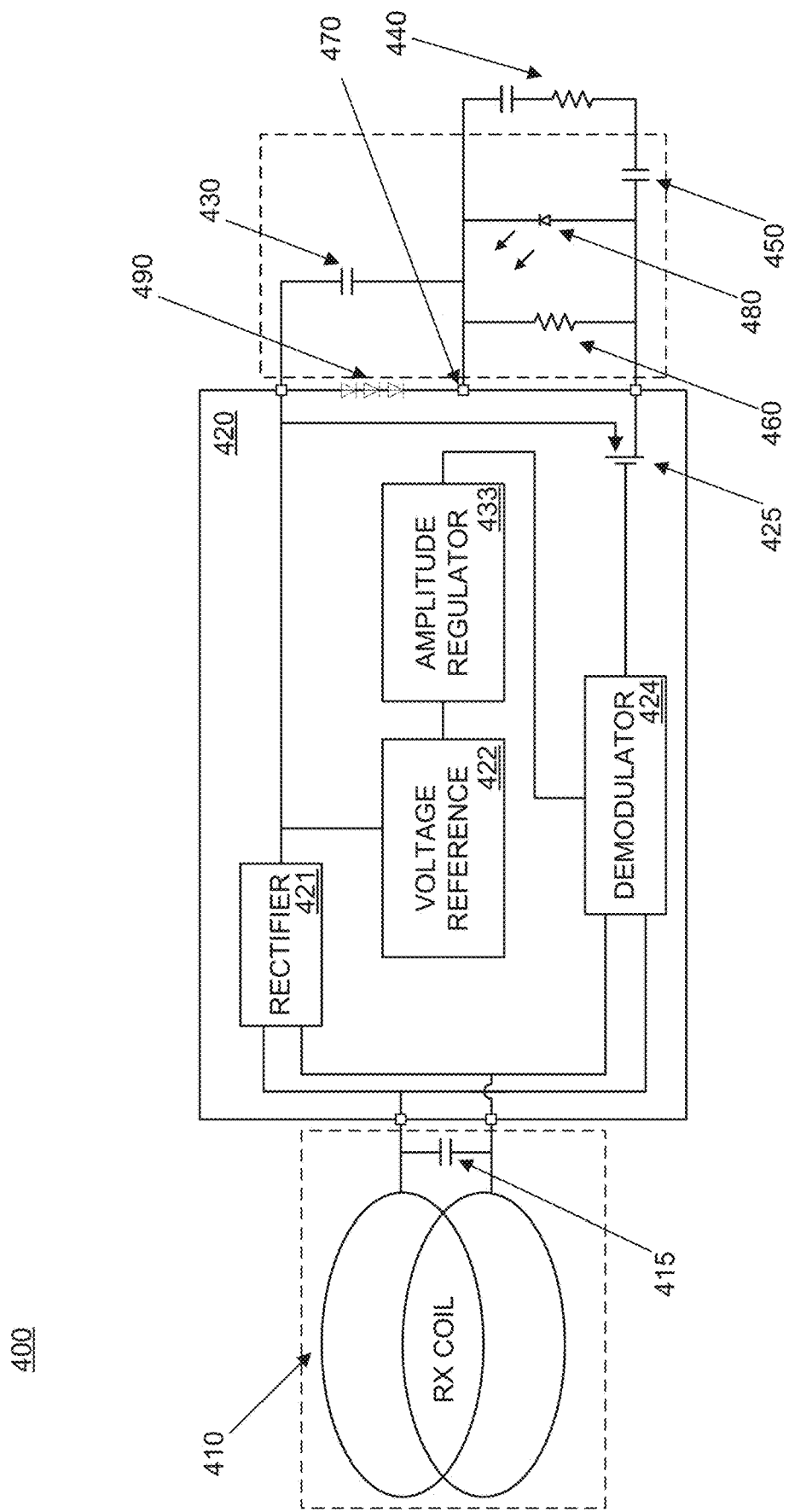
FIG. 4 is a circuit diagram for a wirelessly powered, leadless pacemaker in accordance with an embodiment of the invention.

Turning now to FIG. 4, a circuit diagram of an example implementation of a WPLP in accordance with an embodiment of the invention is illustrated. WPLP includes a receiver coil 410 connected to microchip 420. In numerous embodiments, the receiver coil is resonantly coupled to the transmitter coil of a controller. A magnetic field produced by the transmitter coil can induce current in the receiver coil. In many embodiments, the receiver coil is coupled to an optional tuning capacitor, $C_{tune}$, 415 targeting a selected operating band to cause resonance and increase the efficiency of power transfer. In various embodiments, the receiver coil is a copper trace on a polyimide substrate featuring a double-layer structure with 6 turns on both sides. However, any number of different receiver coils can be used that are capable of electromagnetic power transfer as appropriate to the requirements of specific applications of embodiments of the invention. Indeed, In many other embodiments, a dipole antenna may be used at the receiver to harvest electromagnetic energy. One of ordinary skill in the art will appreciate that any number of different transmitters and receivers can be used to transfer power without departing from the scope or spirit of the invention.

Microchip 420 includes a rectifier 421 which resonates with the receiver coil and stores charge in a storage capacitor, $C_{sto}$, 430. A voltage reference circuit 422 connected to rectifier 421 generates a stable reference voltage. An amplitude regulator 433 regulates the voltage of output stimulations, and a demodulator 424 controls the rate and/or intensity of the output stimulations via switch 425. When the switch is closed, electrode 440 can electrically stimulate nearby heart tissue, and the output stimulation is delivered through a DC-block capacitor, $C_{blk}$, 450 for charge neutralization. A discharge resistor, $R_{dis}$, 460 nulls the accumulated charge on $C_{blk}$. Node 470 is a connection to the substrate of the microchip to act as a ground.

In many embodiments, a light-emitting diode 480 is included to visually indicate when a stimulation is delivered in order to confirm operation. In various embodiments, a series of safety diodes 490 are added such that when the supply voltage exceeds a threshold value, a discharge path is enabled to rapidly discharge the excess incident charge. While three safety diodes are illustrated in FIG. 4, any number of safety diodes can be added to manage the threshold value as appropriate to the requirements of specific applications of embodiments of the invention. In numerous embodiments, the threshold value varies depending on the tissue to be stimulated. In many embodiments, no safety diodes and/or confirmation LEDs are present. Further, in various embodiments, demodulators decode control information and trigger stimulation in accordance with the control information. In numerous embodiments, additional circuitry may be included which records information about the heart and transmits it via a transmission circuit to the controller and/or a different device to enable monitoring of heart function.

Figure 5:
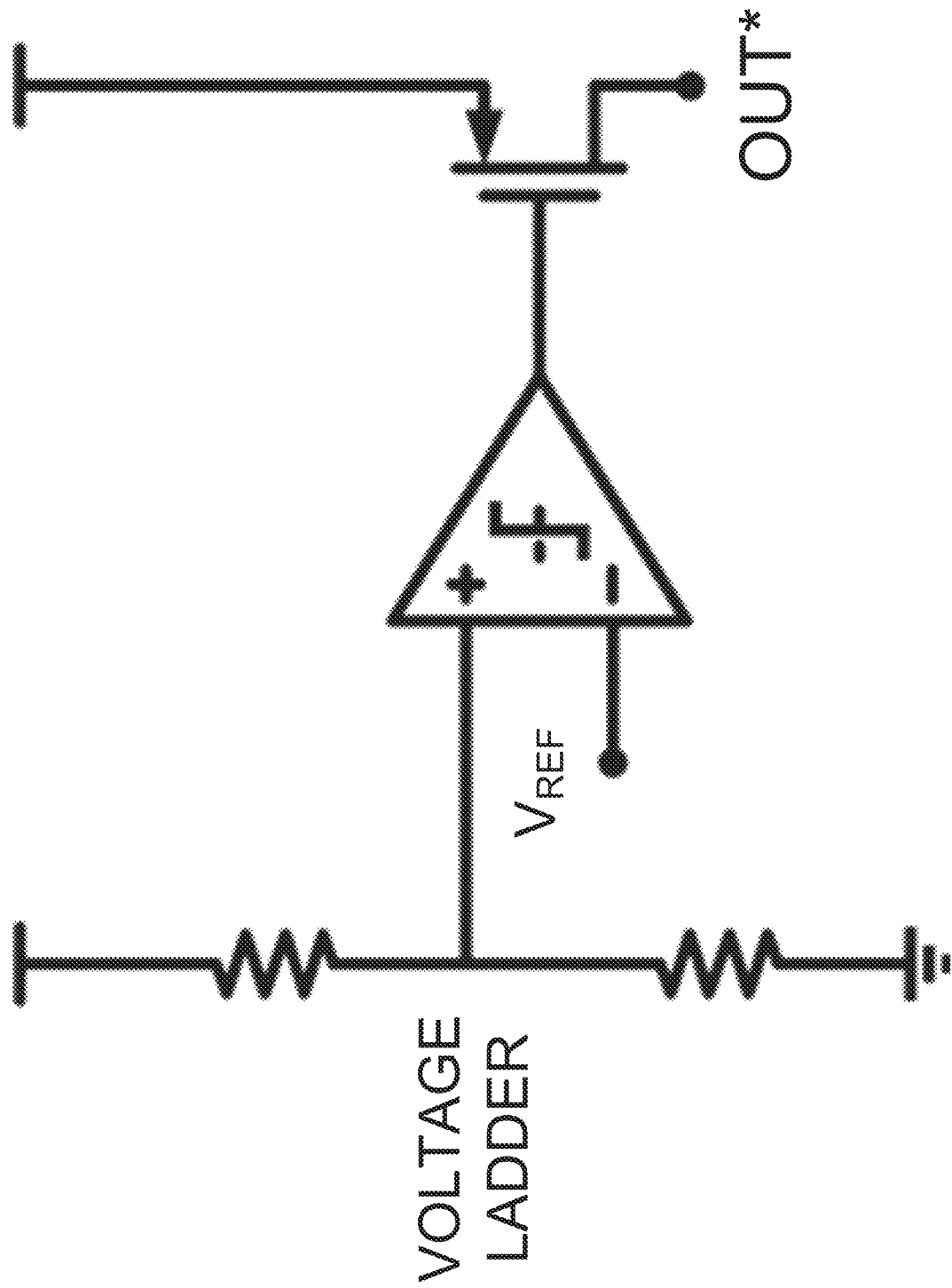
FIG. 5 is a circuit diagram for a low-dropout circuit in accordance with an embodiment of the invention.

With particular respect to the voltage reference and amplitude regulator blocks, any number of different circuits can be used as appropriate to the requirements of specific applications of embodiments of the invention. For example, low-dropout (LDO) circuits can be used to regulate supply voltage. However, LDO circuits tend to have high static power consumption. An example circuit schematic for a modified LDO circuit with reduced power requirements in accordance with an embodiment of the invention is illustrated in FIG. 5. The lower bar of the pulse amplitude of the signal can be lowered by comparing a fraction of the supply voltage with a reference voltage ($V_{REF}$). If the supply voltage is lower than a given threshold voltage, the demodulator block can be disabled. In numerous embodiments, an LED at the output of the LDO circuit can regulate an upper voltage boundary. In many embodiments, the modified LDO circuit can operate with on the order of 0.1 nanoamps of current. While a particular LDO circuit is illustrated in FIG. 5, any number of different architectures, including alternatives to LDOs can be utilized as appropriate to the requirements of specific applications of embodiments of the invention.

Figure 6A:
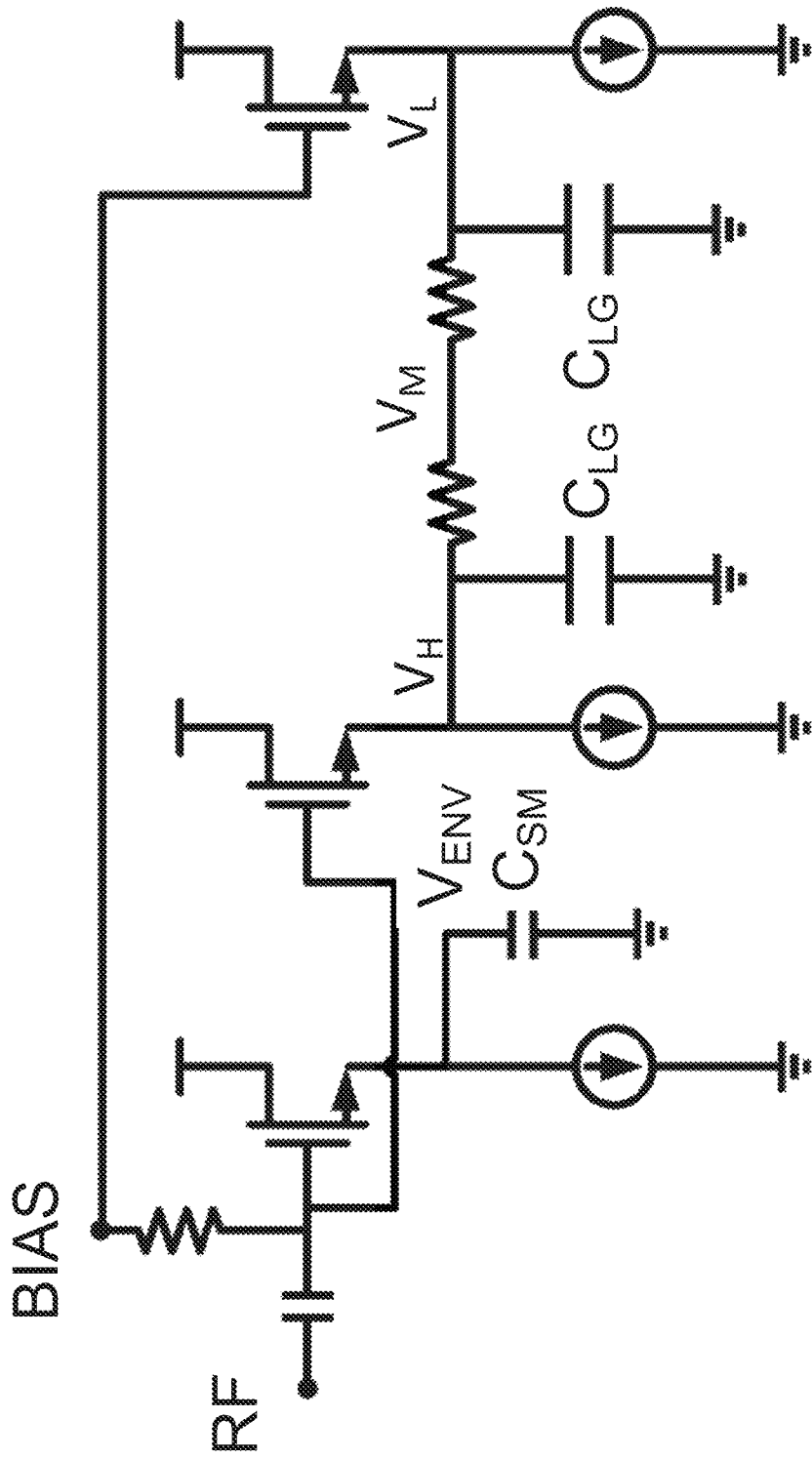
FIG. 6A is a circuit diagram for a demodulator in accordance with an embodiment of the invention.
Figure 6C:
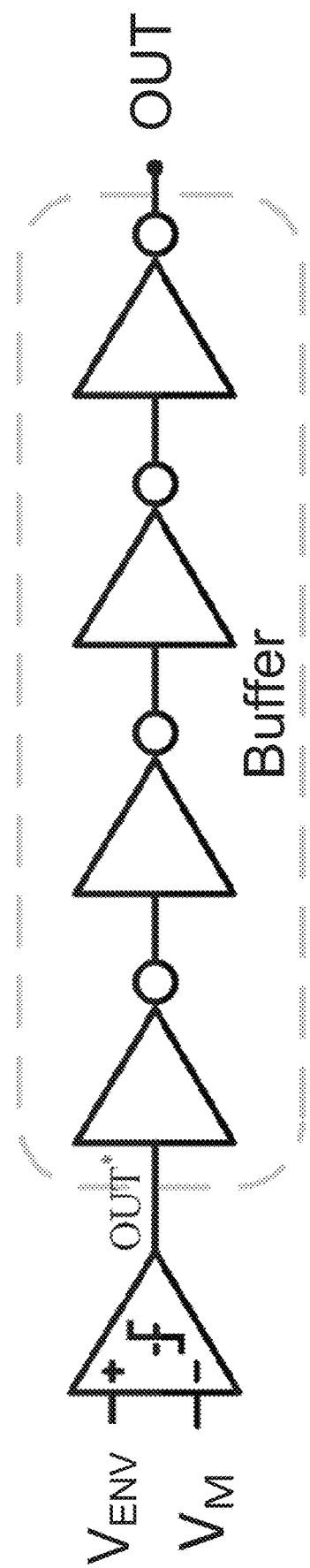
FIG. 6C is a circuit diagram for a buffer circuit in accordance with an embodiment of the invention.

With further attention to the demodulator block, again any number of different demodulator circuitries can be utilized depending on the control scheme to be utilized. A particular example demodulator circuit in accordance with an embodiment of the invention in FIG. 6A. In the illustrated embodiment, the demodulator circuitry includes three source follower replicas. High end, low end, and transient envelope signals are extracted, denoted as $V_H$, $V_L$, and $V_{ENV}$, respectively. The $V_{ENV}$ detection branch uses a relatively small capacitor, $C_{SM}$, while $V_H$ and $V_L$ are extracted on larger capacitors with and without the AC input, respectively. Because of the nonlinearity of the CMOS transistors' transfer characteristics, an AC swing applied on a constant gate bias generates a larger source voltage. The average of $V_H$ and $V_L$, $V_M$, is obtained through a resistive divider, which is thereafter compared with $V_{ENV}$ to construct the timing of the output pulse. An example waveform illustrating the voltages of nodes in the circuit in accordance with an embodiment of the invention in FIG. 6B. In many embodiments, a buffer circuit can be added after the demodulator circuit to sharpen the recovered timing signal. An example buffer circuit in accordance with an embodiment of the invention is illustrated in FIG. 6C. While particular circuits for demodulator circuitries and buffer circuitries are illustrated in FIGS. 6A and 6C, any number of circuit architectures can be used as appropriate to the requirements of specific applications of embodiments of the invention.

In various embodiments, the WPLP can be encapsulated by, or portions otherwise coated with, hyrdrogels. Hydrogels are materials whose properties such as toughness, stickiness, bioactivity, conductiveness, and other properties can be tuned using different stimuli. These stimuli are specific to the composition of the specific hydrogel, and can include, but are not limited to, mechanical, electrical, optical, thermal, and/or chemical stimuli. In numerous embodiments, hydrogels can harbor chemicals, including drugs, become electrically conductive, and/or be magnetically active. By encasing WPLPs in hydrogels, better interfacing with nearby tissues can be achieved.

Figure 7:
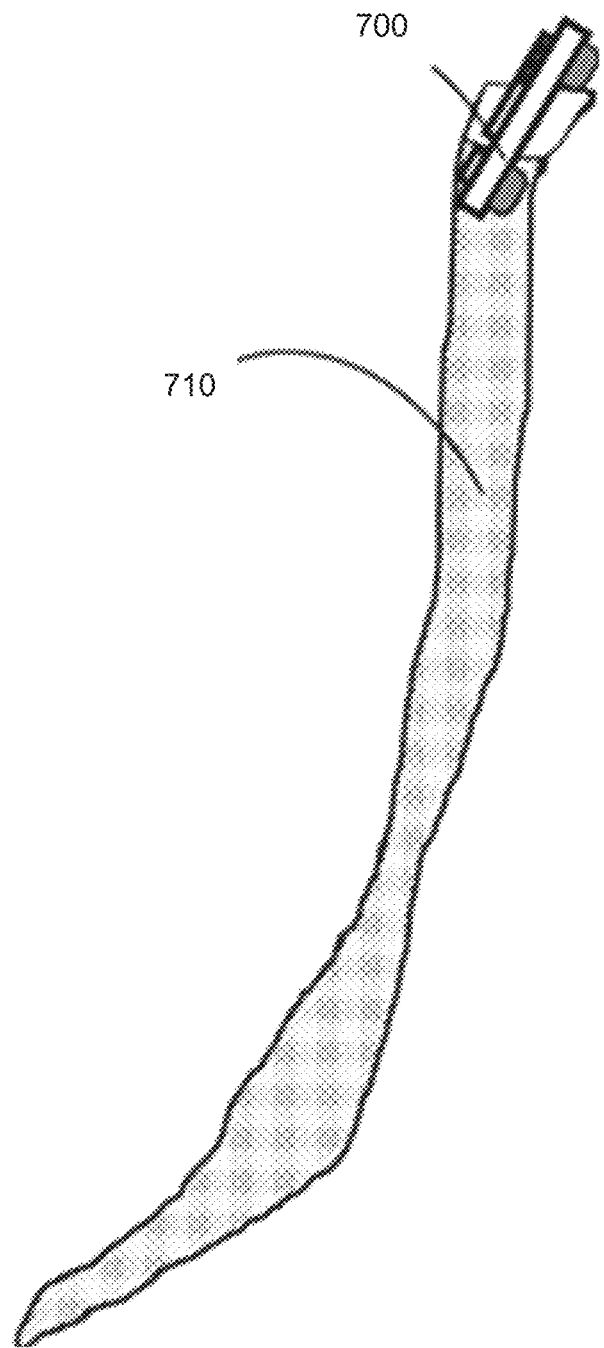
FIG. 7 illustrates a blood vessel utilized as an antenna for a wirelessly powered, leadless pacemaker in accordance with an embodiment of the invention.

Furthermore, in many embodiments, nearby biological structures can be coated in hydrogels. For example, a vein or artery may be filled with and/or coated with a hydrogel which is magnetically active. The hydrogel can then be connected to the receiver coil in order to extend the wireless power transfer capabilities. In some embodiments, the hydrogel can be electrically and/or magnetically active and used as an antenna for transmitting signals from the WPLP. An example of a blood vessel filled with a hydrogel acting as an antenna is illustrated in accordance with an embodiment of the invention in FIG. 7. A WPLP 700 is placed into or abutting a blood vessel 710 which is then coated and/or filled with hydrogel. Indeed, there are any number of uses for hydrogels in conjunction with WPLPs, including, but not limited to, providing more stable anchor points for WPLPs, providing a controllable drug delivery mechanism, insulating WPLPs, acting as an electrode for extended myocardial capture during pacing, providing chemical and/or molecular sensing, and/or any of number of other functionalities as appropriate to the requirements of a specific application of an embodiment of the invention.

Furthermore, in many embodiments, a biocompatible electrode material with proper range of impedance values can be used to deliver current to the heart tissue or vein. Examples of electrode materials include, but are not limited to, Gold, Platinum, Gold-Iridium, Platinum-Iridium, PEDOT, and/or any other material suited for delivering electrical stimulation as appropriate to the requirements of specific applications of embodiments of the invention.

While a particular circuitries for WPLPs are illustrated in accordance with an embodiment of the invention in FIGS. 4, 6A, and 6C, one of ordinary skill in the art can appreciate that any number of different architectures can be used without departing from the scope or spirit of the invention. Control schemes and processes for utilizing WPLPs are discussed in more detail below.

Control Schemes

Control schemes refer to the number and types of power transfer signals utilized to control a given set of WPLPs. In numerous embodiments, RF induction or resonance inductive coupling is used to wirelessly power WPLPs. In various embodiments, WPLPs are powered using other wireless power transfer methodologies, including, but not limited to, other nonradiative techniques or radiative techniques. With particular reference to RF induction, as the magnetic field is generated by running an RF current through a coil, the "power transfer signal" refers to the RF waveform which is directly translated into the changes in the magnetic field, and thus the current at the receiver coil. As such, the power transfer signal can be transmitted via RF induction. Similarly, power transfer signals in a radiative wireless power transfer system can be understood to be the radiating electromagnetic wave. The power transfer signal can be modulated in order to directly control WPLPs.

Depending on the number of WPLPs that need to be controlled, different control schemes can be utilized. In numerous embodiments, the basic control scheme for controlling a single WPLP enables charging over a long period of time using a low power, power transfer signal. However, in various embodiments, the basic control scheme can be modified to control multiple WPLPs using a single frequency power transfer signal, or multiple power transfer signals at different frequencies, both of which are discussed below.

Figure 8:
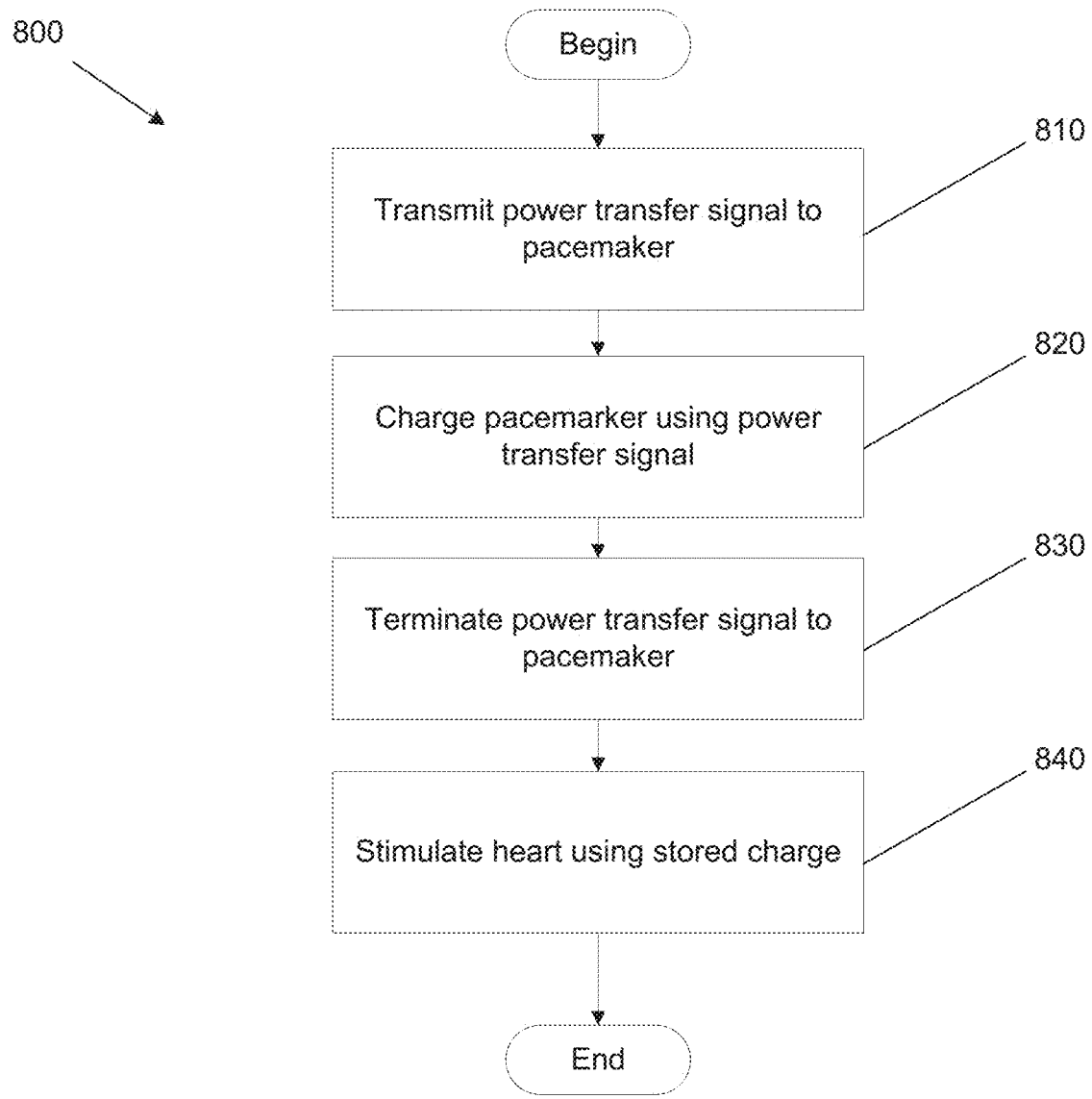
FIG. 8 is a flow chart of a process for a basic control scheme for wirelessly powered, leadless pacemakers in accordance with an embodiment of the invention.

In many embodiments, a basic control scheme involves a single WPLP which controlled using a pulse modulated power transfer signal. A basic control scheme in accordance with an embodiment of the invention is illustrated in FIG. 8. Basic control scheme 800 includes transmitting (810) a power transfer signal to a WPLP at a particular frequency. The WPLP is charged (820) using the power transfer signal while it is being transmitted. When the power transfer signal is terminated (830), the WPLP discharges the stored power to stimulate (840) the heart tissue.

Figure 9:
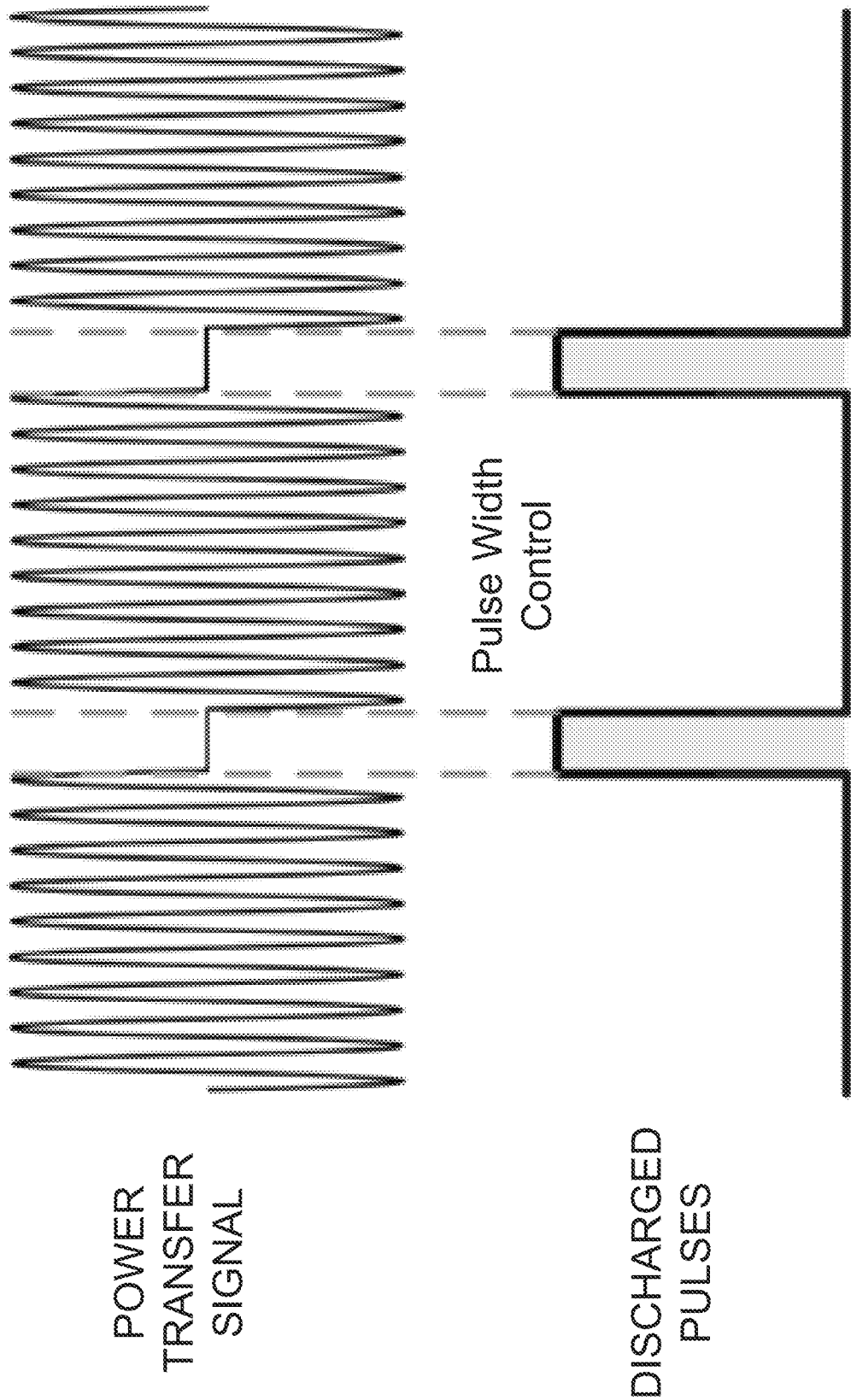
FIG. 9 illustrates an example power transmission signal and the corresponding stimulation pulses in accordance with an embodiment of the invention.

An example power transfer signal for a basic control scheme in accordance with an embodiment of the invention is illustrated in FIG. 9. The power transfer signal (top) is a regular, periodic signal interrupted by periods of zero amplitude. The resulting discharged stimulation pulses from the WPLP are triggered by the zero amplitude gaps. This basic control scheme can confer significant gains in energy efficiency over a WPLP which requires all power to be immediately discharged.

Figure 10:
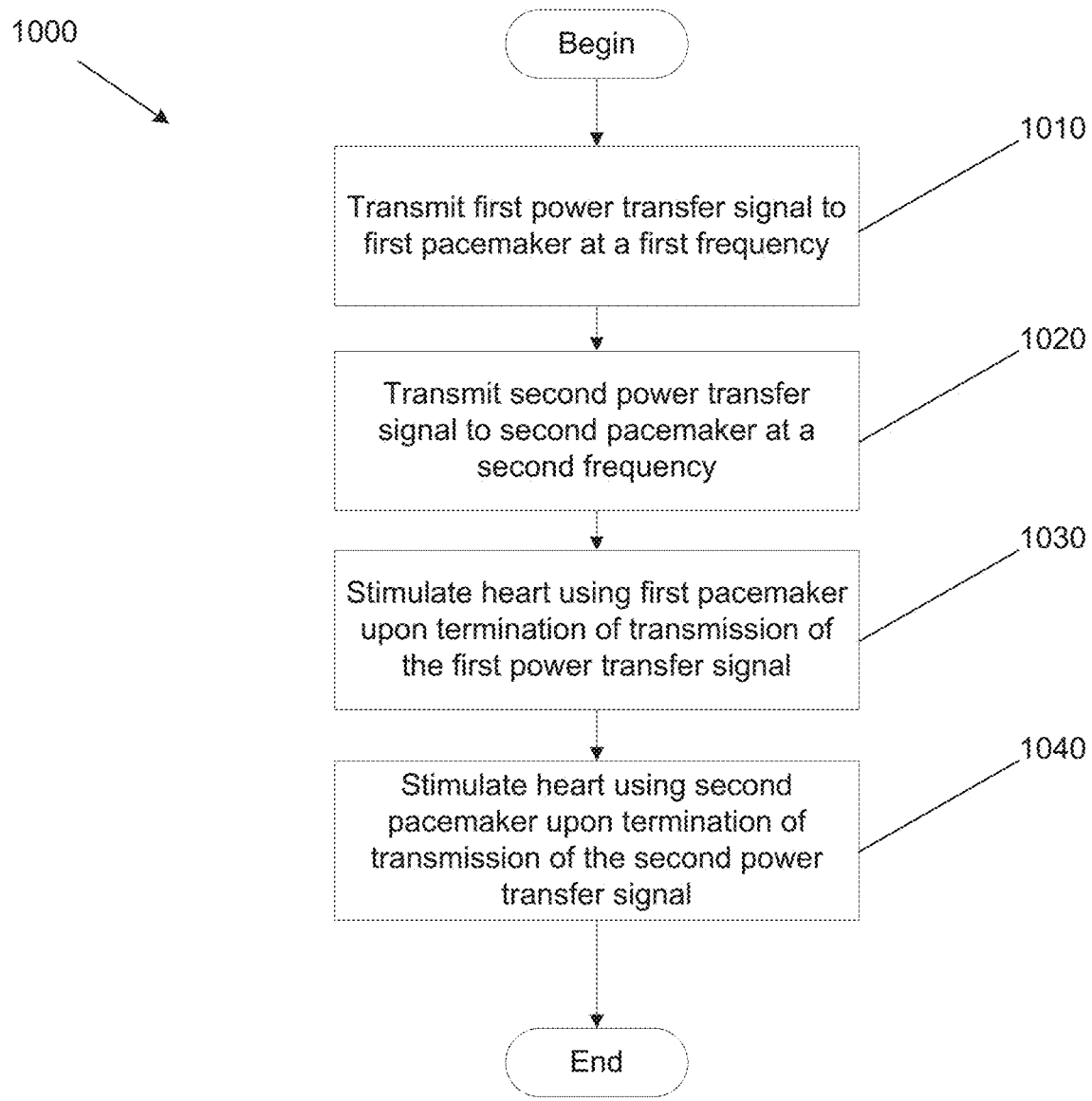
FIG. 10 is a flow chart of a process for controlling multiple wirelessly powered, leadless pacemakers using multiple power transmission signals in accordance with an embodiment of the invention.

The basic control scheme can be built upon in any of a number of ways. For example, multiple iterations of the basic control scheme can be used simultaneously using a frequency division control scheme. By utilizing a different frequency for different sets of WPLPs (or each individual WPLP), and by tuning the respective WPLPs to their particular frequency, a controller can control multiple WPLPs. A frequency division control scheme in accordance with an embodiment of the invention is illustrated in FIG. 10.

Frequency division control scheme 1000 includes transmitting (1010) a first power transfer signal to a first WPLP at a first frequency, and transmitting (1020) a second power transfer signal to a second WPLP at a second frequency. Similar to the basic control scheme, when the first power transfer signal is terminated (1030) the first WPLP is triggered to discharge, and when the second power transfer signal is terminated (1040) the second WPLP is triggered to discharge. In this way, a controller capable of transmitting multiple simultaneous signals can be used to control multiple WPLPs. In various embodiments, controllers can synchronize the discharges of multiple WPLPs in a therapeutic manner.

Figure 11:
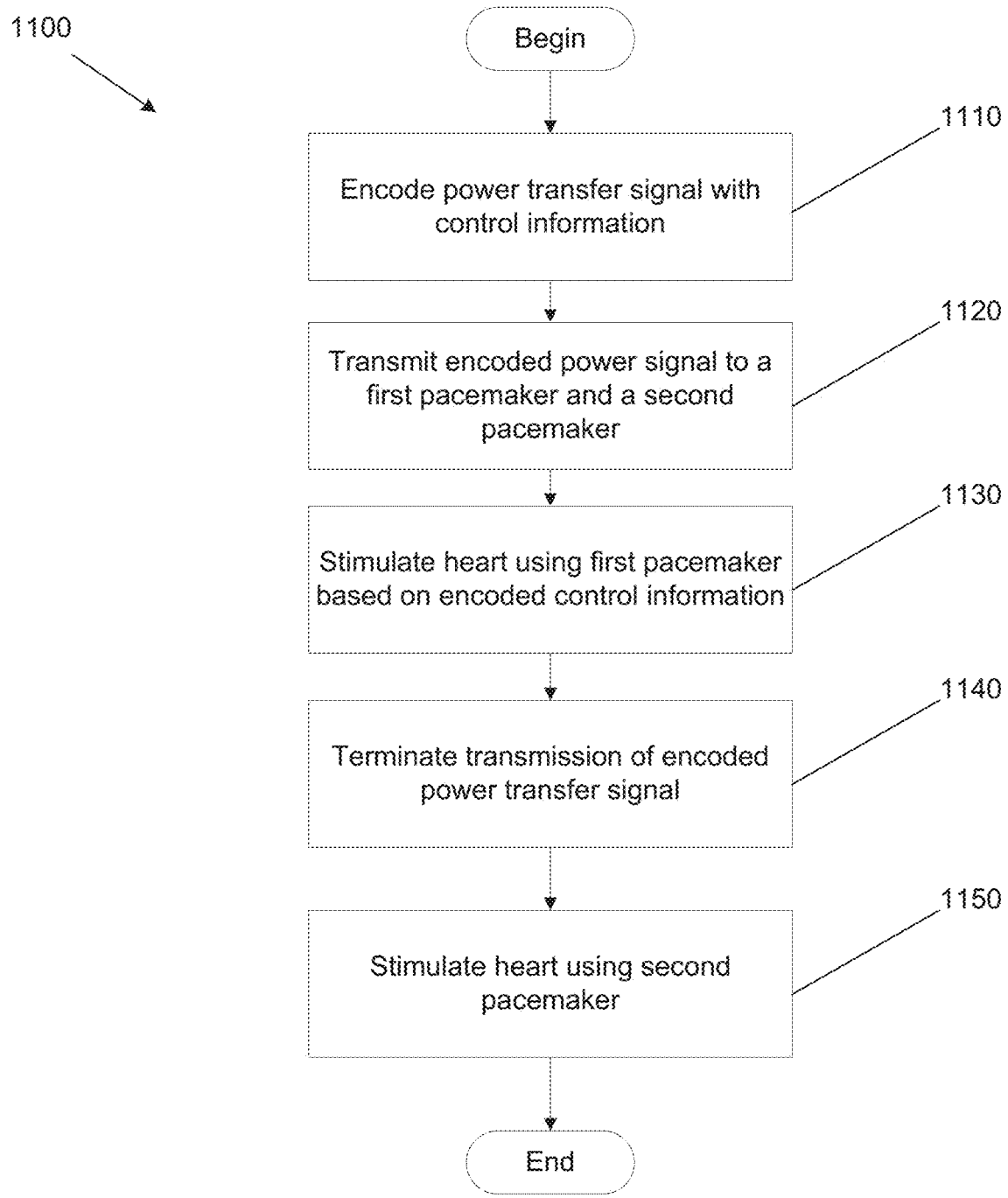
FIG. 11 is a flow chart of a process for pacing a heart with multiple wirelessly powered, leadless pacemakers using a single power transmission signal in accordance with an embodiment of the invention.

However, in many situations, it can be desirable to reduce the total number of frequencies being utilized. In many embodiments, a label division control scheme can be utilized whereby the power transfer signal is modulated with control information. For example, WPLPs can be assigned unique labels which can be encoded into the power transfer signal to indicate that the designated WPLP should begin firing. In this way, a first WPLP can be triggered to fire before a second WPLP as appropriate to a particular therapeutic stimulation pattern. An example label division control scheme in accordance with an embodiment of the invention is illustrated in FIG. 11.

Label division control scheme 1100 includes encoding (1110) a power transfer signal with control information, and transmitting (1120) the label encoded power transfer signal to both a first and a second WPLP. After charging, but while the power transfer signal is still being transmitted, the heart tissue is stimulated (1130) using the first WPLP based on the encoded control information. The transmission of the label encoded power transfer signal is terminated (1140), and the heart is stimulated (1150) using the second WPLP. However, the label division control scheme illustrated in FIG. 11 is one of many different embodiments of a label division control scheme. Any number of different label division control schemes can be generated by selecting and implementing commands that are encodable into the power transfer signal. Indeed, in many embodiments, some WPLPs may not need to decode power transfer signals in a label division scheme, instead relying upon a basic control scheme. WPLPs under a code division scheme can then be separately controlled to regulate the synchronization.

Indeed, any number of different complex control schemes for multiplexing power transfer can be constructed, including, but not limited to, time division schemes, code division schemes, and/or other complex code divisions schemes that utilize different modulation schemes, and/or any other multiplexing process as appropriate to the requirements of specific applications of embodiments of the invention. In various embodiments, additional circuitry can be added to WPLPs to enable more complex control schemes such as, but not limited to, counters, clock circuitries, decryption circuits, and/or any other circuits as appropriate to the requirements of specific applications of embodiments of the invention. One of ordinary skill in the art will appreciate that different multiplexing techniques can be used while still providing the increase in efficiency provided by WPLPs described herein without departing from the scope or spirit of the invention. Treatments using WPLPs are described in further detail below.

WPLP-Based Treatment

WPLPs can be used in treatment of any of a number of different cardiac conditions. An advantage to WPLPs described herein is that synchronization of WPLPs enables more complex treatment. For example, in many embodiments, different WPLPs can be triggered to fire in a particular pattern with particular respective voltages in response to an arrhythmia until the arrhythmia is extinguished. In some embodiments, WPLPs are capable of producing biphasic and/or monophasic waveforms. Further, WPLPs can be implanted both onto to, and/or into the cardiac tissue. Consequently, WPLPs are highly flexible and can be placed at a medical professional's discretion in order to treat any of a number of different conditions. A set of non-exhaustive example treatments are described below:

A. Cardiac Resynchronization therapy

In some embodiments, two or more WPLPs can be placed on the right and the left ventricles. The WPLPs can be powered to provide stimulation all at once or with an inter-pacemaker delay. This delay can be pre-determined and programmed or can change over time using control information. The delay can vary from 0 to about 200 msec. In various embodiments, the WPLP(s) in the left ventricle can pace at the same time as, earlier than, or later than the WPLP(s) in the right ventricle.

B. Defibrillation:

In some embodiments, two or more WPLPs can be placed on the left and right atrium to treat arrhythmia. Two or more WPLPs can be delivered into the vein of marshall that wraps across the left atrium. In other embodiments, two or more WPLPs can be placed endocardially in the right atrium and the left atrium. In some embodiments, a combination of WPLPs placed endocardially and epicardially can be used to provide defibrillation.

In various embodiments, two or more WPLPs placed in the left and right ventricles can be used to extinguish ventricular arrhythmia. In some embodiments, two or more WPLPs can be delivered into the coronary sinus that traverses across the boundary of the left atrium and the left ventricle. In numerous embodiments, two or more WPLPs can be placed endocardially in the right ventricle and the left ventricle.

C. Conduction Velocity:

In some embodiments, two or more WPLPs can be used to treat re-entrant arrhythmias caused by myocardial scarring. In various embodiments, two or more WPLPs can be placed across a ventricular scar to provide synchronous pacing. Sensed signals on one side can control rate and timing of pacing. Re-entrant arrhythmias can be extinguished by creating refractory myocardial tissue by capturing the myocardium earlier than an incoming wavefront.

In many embodiments, implantable medical devices in the form of sensing nodes (or wired sensing elements) used in conjunction with WPLPs can compute the change in conduction velocity with the on-set of re-entry. The sensing nodes can be used for specific up-titration of conduction velocity in real-time.

D. Mapping of Rotors:

In some embodiments, sensing nodes can be distributed across the atrium to map rotors that lead to atrial fibrillation. In some embodiments, the sensed data can be processed locally or on a device placed elsewhere in the body or kept externally to the body (extracorporeally) to compute dominant frequency, organization index and/or other metrics. These metrics can contribute to mapping arrhythmia in the atrium and can contribute to therapy that extinguishes these abnormal rhythms.

E. Real-Time Mapping:

In various embodiments, sensing nodes can be distributed across either of, or both, the atrium and the ventricle to provide real-time sensed information for creating real-time mapping. The data collected from the sensing nodes can be processed locally on the nodes, or on a device place inside or outside of the body, or on a device external to the body.

F. On-Demand Treatment

Indeed, while particular different treatments are described above, any of them can be performed using different numbers of WPLPs implanted into different locations as appropriate to the patient and at the discretion of attending medical professionals. Further, given the controllable nature of WPLPs, treatment can be delivered on-demand outside of a medical setting. For example, in numerous embodiments, a controller can be carried with a patient who, when an arrhythmia is detected either by the patient themselves or by a sensing device, can trigger the controller to enact treatment of the arrhythmia as it occurs.

In many embodiments, the controller is implemented using a smartphone, whereby inductive power transfer coils of the smartphone can be held to the chest in order to power the WPLPs on demand. In various embodiments, the smartphone can be programmed with appropriate responses which can be selected either by a patient, a medical professional, or automatically. However in numerous embodiments, the controller is a purpose-built controller device.

In various embodiments, controllers are implanted into the patient at a location that is relatively easy to access. In many embodiments, controllers are implanted subcutaneously. Further, additional control devices can be used to link with and remotely command implanted controllers.

Although specific methods for synchronized heart stimulation are discussed above, many different fabrication methods can be implemented in accordance with many different embodiments of the invention. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A heart stimulation system, comprising:
 a controller, comprising:
  at least one wireless power signal generator configured to generate at least one power transfer signal;
  at least one wireless power transmitter configured to transmit the at least one power transfer signal;
  a memory containing a stimulation control application; and
  a processor configured to execute the stimulation control application to generate and transmit the at least one power transfer signal; and
 one or more wirelessly powered, leadless pacemakers (WPLPs), each WPLP comprising:
  a wireless power receiver configured to receive a power transfer signal from the at least one power transfer signal;
  an energy harvesting circuitry configured to store energy from the received power transfer signal; and a stimulation circuitry configured to deliver the stored energy via a stimulation electrode which is triggered by a zero-amplitude gap in the power transfer signal.

2. The heart stimulation system of claim 1, wherein the at least one wireless power transmitter is a near field resonant coupling based transmitter coil and the wireless power receiver is a near field resonant coupling based receiver coil.

3. The heart stimulation system of claim 1, wherein the at least one wireless power transmitter is a far field propagating electromagnetic wave receiver antenna and the wireless power receiver is a far field propagating electromagnetic wave transmitter antenna.

4. The heart stimulation system of claim 1, wherein the one or more WPLPs includes a first WPLP and a second WPLP, and wherein:
a first wireless power receiver of the first WPLP is tuned to a first frequency;
a second wireless power receiver of the second WPLP is tuned to a second frequency; and
the stimulation control application is executable by the processor to cause the at least one wireless power signal generator and the at least one wireless power transmitter to generate and transmit a first power transfer signal at the first frequency and a second power transfer signal at the second frequency.

5. The heart stimulation system of claim 4, wherein the stimulation control application is executable by the processor to time the transmission of the first power transfer signal and the second power transfer signal such that stimulation by the first WPLP and the second WPLP provide stimulation at a determined time relative to each other.

6. The heart stimulation system of claim 4, wherein the at least one wireless power transmitter comprises a first wireless power transmitter configured to transmit at the first frequency, and a second wireless power transmitter configured to transmit at the second frequency; and
wherein the first frequency and the second frequency are selected such that the first wireless power transmitter does not couple with the second wireless power receiver, and the second wireless power transmitter does not couple with the first wireless power receiver.

7. The heart stimulation system of claim 1, wherein the one or more WPLPs includes a first WPLP and a second WPLP, and wherein:
a first wireless power receiver of the first WPLP and a second wireless power receiver of the second WPLP are tuned to a first frequency;
the stimulation control application is executable by the processor to encode a power transfer signal at the first frequency with first control information associated with a first unique label assigned to the first WPLP and with second control information associated with a second unique label assigned to the second WPLP; and
wherein the first control information indicates when the first WPLP delivers stored energy of the first WPLP and the second control information indicates when the first WPLP delivers stored energy of the second WPLP.

8. The heart stimulation system of claim 1, wherein the at least one wireless power transmitter includes a wireless power transmitter that is tunable to a plurality of frequencies.

9. The heart stimulation system of claim 1, wherein the controller is an extracorporeal device.

10. The heart stimulation system of claim 1, wherein the controller is configured to be implanted subcutaneously.

11. The heart stimulation system of claim 1, wherein the one or more WPLPs includes a first WPLP and a second WPLP and the first WPLP is configured to stimulate a first chamber of a heart and the second WPLP is configured to stimulate the first chamber of the heart.

12. The heart stimulation system of claim 1, wherein the one or more WPLPs includes a first WPLP and a second WPLP and the first WPLP is configured to stimulate a first chamber of a heart, and the second WPLP is configured to stimulate a second chamber of the heart.

13. The heart stimulation system of claim 1, wherein the one or more WPLPs includes a first WPLP configured to stimulate a blood vessel in order to deliver an electrical stimulation to a heart.

14. The heart stimulation system of claim 1, wherein the one or more WPLPs includes a first WPLP and a second WPLP and the first WPLP is configured to stimulate a chamber of a heart, and the second WPLP is configured to stimulate a blood vessel in order to deliver an electrical stimulation to the heart.

15. The heart stimulation system of claim 1, wherein:
the one or more WPLPs includes a first WPLP comprising sensing circuitry and the transmission of the at least one power transfer signal induces the first WPLP to deliver an electrical therapy to a heart in order to maintain a normal heart condition; and
the sensing circuitry of the first WPLP is configured to sense heart activity.

16. The heart stimulation system of claim 1, wherein the WPLP includes sensing circuitry configured to sense and/or monitor biological activity, including heartbeats, temperature, blood flow, and/or motion.

17. The heart stimulation system of claim 16, wherein the wireless power receiver of the WPLP is configured to transmit the sensed biological activity to the controller.

18. The heart stimulation system of claim 1, wherein:
the at least one wireless power transmitter includes transmission coils, RF signal generators, and/or antennas configured to generate a magnetic field;
the wireless power receiver includes at least one coil; and
the at least one power transmitter and the wireless power receiver perform inductive power transfer using radio-frequency induction.

19. The heart stimulation system of claim 18, wherein the at least one power transmitter and wireless power receiver coils are actively tuned to a resonant frequency.

20. The heart stimulation system of claim 1, further comprising a hydrogel encapsulating and/or coating at least a portion of the WPLP, wherein the hydrogel is electrically conductive and/or magnetically active.

21. The heart stimulation system of claim 20, wherein the hydrogel is configured to operate as an antenna of the WPLP.

* * * * *